United States Patent
Beasley et al.

(10) Patent No.: US 7,094,881 B2
(45) Date of Patent: Aug. 22, 2006

(54) ISOLATED HUMAN PROTEASE PROTEINS, NUCLEIC ACID MOLECULES ENCODING HUMAN PROTEASE PROTEINS, AND USES THEREOF

(75) Inventors: Ellen M Beasley, Darnestown, MD (US); Zhenya Li, Rockville, MD (US)

(73) Assignee: Applera Corporation, Norwalk, CT (US)

( * ) Notice: Subject to any disclaimer, the term of this patent is extended or adjusted under 35 U.S.C. 154(b) by 482 days.

(21) Appl. No.: 10/640,326

(22) Filed: Aug. 14, 2003

(65) Prior Publication Data

US 2004/0038896 A1 Feb. 26, 2004

Related U.S. Application Data

(62) Division of application No. 10/224,414, filed on Aug. 21, 2002, now Pat. No. 6,638,751, and a division of application No. 09/934,551, filed on Aug. 23, 2001, now Pat. No. 6,461,850.

(60) Provisional application No. 60/226,903, filed on Aug. 23, 2000.

(51) Int. Cl.
*C07K 16/00* (2006.01)
*C12P 21/08* (2006.01)

(52) U.S. Cl. .............. 530/387.1; 530/387.3; 530/388.1; 530/388.26; 530/389.1

(58) Field of Classification Search .................. None
See application file for complete search history.

(56) References Cited

OTHER PUBLICATIONS

Vogt, G., Stocker, W., Storch, V., and Zwilling, R. Biosynthesis of Astacus protease, a digestive enzyme from crayfish (1989) Histochemistry vol. 91, pp. 373-381.*
Yasumasu, S., Katow, S., Hamazaki, T.S., Iuchi, I., and Yamagami, K. Two constituent proteases of a teleostean hatching enzyme: concurrent syntheses and packaging in the same secretory granules in discrete arrangement (1992) Developmental Biology, vol. 149, pp. 349-356.*

* cited by examiner

*Primary Examiner*—Marianne P. Allen
*Assistant Examiner*—Ian Dang
(74) *Attorney, Agent, or Firm*—Celera Genomics; Justin D. Karjala

(57) ABSTRACT

The present invention provides amino acid sequences of peptides that are encoded by genes within the human genome, the protease peptides of the present invention. The present invention specifically provides isolated peptide and nucleic acid molecules, methods of identifying orthologs and paralogs of the protease peptides, and methods of identifying modulators of the protease peptides.

14 Claims, 7 Drawing Sheets

```
  1  ATGGAGGGTG TAGGGGGTCT CTGGCCTTGG GTGCTGGGTC TGCTCTCCTT
 51  GCCAGGTGTG ATCCTAGGAG CGCCCCTGGC CTCCAGCTGC GCAGGAGCCT
101  GTGGTACCAG CTTCCCAGAT GGCCTCACCC CTGAGGGAAC CCAGGCCTCC
151  GGGGACAAGG ACATTCCTGC AATTAACCAA GGGCTCATCC TGGAAGAAAC
201  CCCAGAGAGC AGCTTCCTCA TCGAGGGGGA CATCATCCGG CCGAGTCCCT
251  TCCGACTGCT GTCAGCAACC AGCAACAAAT GGCCCATGGG TGGTAGTGGT
301  GTCGTGGAGG TCCCCTTCCT GCTCTCCAGC AAGTACGATG AGCCCAGCCG
351  CCAGGTCATC CTGGAGGCTC TTGCGGAGTT TGAACGTTCC ACGTGCATCA
401  GGTTTGTCAC CTATCAGGAC CAGAGAGACT TCATTTCCAT CATCCCCATG
451  TATGGGTGCT CTCGAGTGT GGGGCGCAGT GGAGGGATGC AGGTGGTCTC
501  CCTGGCGCCC ACGTGTCTCC AGAAGGGCCG GGGCATTGTC CTTCATGAGC
551  TCATGCATGT GCTGGGCTTC TGGCACGAGC ACACGCGGGC CGACCGGGAC
601  CGCTATATCC GTGTCAACTG GAACGAGATC CTGCCAGGCT TTGAAATCAA
651  CTTCATCAAG TCTCGGAGCA GCAACATGCT GACGCCCTAT GACTACTCCT
701  CTGTGATGCA CTATGGGAGG CTCGCCTTCA GCCGGCGTGG GCTGCCCACC
751  ATCACCACC TTTGGGCCCC CAGTGTCCAC ATCGGCCAGC GATGGAACCT
801  GAGTGCCTCG GACATCACCC GGGTCCTCAA ACTCTACGGC TGCAGCCCAA
851  GTGGCCCCAG GCCCCGTGGG AGAGGTGAGT GGCATGGCAG GAAGGTGACT
901  TGA
```

FEATURES:
Start codon: 1
Stop codon: 901

Homologous proteins:
Top 10 BLAST Hits

|  | Score | E |
|---|---|---|
| gi\|2134006\|pir\|\|C48826 high choriolytic hatching proteinase (EC... | 189 | 3e-47 |
| gi\|2190297\|dbj\|BAA12146.1\| (D83950) choriolysin H [Oryzias lati... | 188 | 6e-47 |
| gi\|399868\|sp\|P31581\|HCE2_ORYLA HIGH CHORIOLYTIC ENZYME 2 PRECUR... | 187 | 1e-46 |
| gi\|399867\|sp\|P31580\|HCE1_ORYLA HIGH CHORIOLYTIC ENZYME 1 PRECUR... | 187 | 1e-46 |
| gi\|400172\|sp\|P31579\|LCE_ORYLA LOW CHORIOLYTIC ENZYME PRECURSOR ... | 184 | 1e-45 |
| gi\|2190298\|dbj\|BAA20403.1\| (D83949) choriolysin L [Oryzias lati... | 180 | 1e-44 |
| gi\|1168541\|sp\|P42662\|ASTL_COTJA ASTACIN LIKE METALLOENDOPEPTIDA... | 165 | 6e-40 |
| gi\|2252655\|gb\|AAB62737.1\| (U62621) nephrosin precursor [Cyprinu... | 164 | 1e-39 |
| gi\|2828509\|sp\|P42664\|UVS2_XENLA EMBRYONIC PROTEIN UVS.2 PRECURS... | 157 | 2e-37 |
| gi\|2661464\|emb\|CAA05969.1\| (AJ003190) astacus egg astacin [Asta... | 155 | 4e-37 |
| gi\|1730897\|sp\|P55112\|YPD6_CAEEL HYPOTHETICAL ZINC METALLOPROTEI... | 153 | 3e-36 |
| gi\|7498742\|pir\|\|T20658 hypothetical protein F09E8.6 - Caenorhab... | 152 | 3e-36 |
| gi\|1723350\|sp\|P55115\|YC92_CAEEL HYPOTHETICAL ZINC METALLOPROTEI... | 151 | 8e-36 |

EST:
gi\|2166389\|gb\|AA452720.1\|AA452720 zx39d07.r1 Soares_total_fetus...  46  0.020
gi\|4136891\|gb\|AI367146.1\|AI367146 qq41e12.x1 Soares_NhHMPu_S1 H...  44  0.078

EXPRESSION INFORMATION FOR MODULATORY USE:
library source:
gi\|2166389\|gb\|AA452720.1     Human fetus
gi\|4136891\|gb\|AI367146.1     Pooled human melanocyte, fetal heart, and pregnant uterus

FIGURE 1

```
  1 MEGVGGLWPW VLGLLSLPGV ILGAPLASSC AGACGTSFPD GLTPEGTQAS
 51 GDKDIPAINQ GLILEETPES SFLIEGDIIR PSPFRLLSAT SNKWPMGGSG
101 VVEVPFLLSS KYDEPSRQVI LEALAEFERS TCIRFVTYQD QRDFISIIPM
151 YGCFSSVGRS GGMQVVSLAP TCLQKGRGIV LHELMHVLGF WHEHTRADRD
201 RYIRVNWNEI LPGFEINFIK SRSSNMLTPY DYSSVMHYGR LAFSRRGLPT
251 ITPLWAPSVH IGQRWNLSAS DITRVLKLYG CSPSGPRPRG RGEWHGRKVT
```

FEATURES:
Functional domains and key regions:
Prosite search results:

| InterPro | Results of FPrintScan against PRINTS | Results of HMMPfam against PFAM-A | Results of PPsearch against PROSITE | Results of ProfileScan against PROSITE profiles |
|---|---|---|---|---|
| IPR000130 Neutral zinc metallopeptidases, zinc-binding region | | | PS00142 [179-188] | |
| IPR001506 Astacin (Peptidase family M12A) family | PR00480 [120-138] [174-192] [193-210] [229-244] [267-280] | PF01400 [92-283] | | |

| IPR000130 | PS00142 | ZINC_PROTEASE | Neutral zinc metallopeptidases, zinc-binding region |
|---|---|---|---|
| IPR001506 | PR00480 | ASTACIN | Astacin (Peptidase family M12A) family |
| | PF01400 | Astacin | |

Membrane spanning structure and domains:
```
  Helix Begin  End   Score Certainty
    1     6    26    1.850 Certain
    2   143   163    0.849 Putative
```

BLAST Alignment to Top Hit:
```
>gi|2134006|pir||C48826 high choriolytic hatching proteinase (EC
        3.4.24.-) HCE21 precursor - Japanese medaka
        Length = 279

Score =  189 bits (475), Expect = 3e-47
 Identities = 106/272 (38%), Positives = 148/272 (53%), Gaps = 8/272 (2%)

Query:  14 LLSLPGVILGAPLASSCAGACGTSFPDGLTPEGTQASGDKDIPAINQGLILEETPESSFL  73
           LL L G+    P+ +    G   +G  EG +    +D     ++        L
Sbjct:  11 LLFLLGIAQALPVQNEEGHEEGNK--EGHGEEGVEEGDEDDFVDFTTRILTSNNNTDQLL  68

Query:  74 IEGDIIRPSPFRLLSATSNK--WPMGGSGVVEVPFLLSSKYDEPSRQVILEALAEFERST 131
           +EGD++  P+     +  N  W   +G V +P+++SS+Y       I  A+  F   T
Sbjct:  69 LEGDLVAPTNRNAMKCWYNSCFWKKASNGFVVIPYVISSQYSRGEVATIEGAMRAFNGRT 128

Query: 132 CIRFVTYQDQRDFISIIPMYGCFSSVGRSGGMQVVSL-APTCLQKGRGIVLHELMHVLGF 190
           CIRFV   ++ DFIS++    GC+S +GR GG Q +SL    C+  G  I+ HEL H LGF
Sbjct: 129 CIRFVRRTNEYDFISVVSKNGCYSELGRKGGQQELSLNRGGCMYSG--IIQHELNHALGF 186

Query: 191 WHEHTRADRDRYIRVNWNEILPGFEINFIKSRSSNMLTPYDYSSVMHYGRLAFS-RRGLP 249
            HE TR+DRD Y+R+NW  I+P  NF K  ++N+ TPYDYSS+MHYGR AFS   G
Sbjct: 187 QHEQTRSDRDSYVRINWQNIIPASAYNFNKHDTNNLNTPYDYSSIMHYGRDAFSIAYGRD 246
```

FIGURE 2A

```
Query: 250 TITPLWAPSVHIGQRWNLSASDITRVLKLYGC 281
            +ITP+   P+V IGQR +S  DITR+  LY C
Sbjct: 247 SITPIPNPNVPIGQRNGMSRWDITRINVLYNC 278
```

Hmmer search results (Pfam):

| Model | Description | Score | E-value | N |
|---|---|---|---|---|
| PF01400 | Astacin (Peptidase family M12A) | 275.0 | 5.9e-84 | 1 |
| CE00424 | E00424 meprin_A | 70.5 | 2.4e-18 | 1 |
| PF00712 | DNA polymerase III beta subunit | 2.9 | 7.8 | 1 |

Parsed for domains:

| Model | Domain | seq-f | seq-t | hmm-f | hmm-t | score | E-value |
|---|---|---|---|---|---|---|---|
| PF00712 | 1/1 | 105 | 121 .. | 376 | 392 .] | 2.9 | 7.8 |
| PF01400 | 1/1 | 92 | 283 .. | 1 | 200 [] | 275.0 | 5.9e-84 |
| CE00424 | 1/1 | 179 | 284 .. | 142 | 252 .. | 70.5 | 2.4e-18 |

FIGURE 2B

```
   1 TTCCCTTCAC TGGGTGCAGG TGACTGTGGG GGTGTCCCCA AATGCTGCCC
  51 AGCGCTGACA TGCTCCGCCT CTGGGATTTC AATCCAGGTG GGGCCCTGAG
 101 TGACCTGGCT CTGGGGCTCA GGGGTATGGA GGAGGGGGGA TATAGGTAAG
 151 GAGTTTAAAT TTCCAAATCT GTGAAATGGG AATAAATACT GACTGATCAT
 201 GCCAGCTGCT GTGGGATTAG GGGGTGGACT CCCTGCGAGG CTCTGGGCAT
 251 CTGGGGGTTC CACCTTTCCC ACATGGCAGG CTTTCTAGGG TGCTGCACAC
 301 TGTTCAGTTT GTGAAATTTC CTGGAGCCCT GTGCTTGTGA TAGTGAACTT
 351 TTCTATATGT GTACTAAAAT AAAAGCTTGT GAAAGTGCAG TGACCTTTTC
 401 CTCCTTCCGG AGATACACGG GGGGCGCCCC AGGGTCTCAG GCAGCTTTCC
 451 CCATGTCTAA GCACAGGCCG GGGTAGGAAA GGGGGTCTCC CTCGCTGGAG
 501 GAATAGGTCT ATACCTGGGC TGGGGCCTCA GCTAGGCCTG GAGCAACTTT
 551 CTGCGATGTT TCTCTGCCCC CTGGAGGCAG GAAGGAACCT CAGAAGAGCC
 601 ACACTCCCAA GCGGGCCCCT CCTGTCTTTC ACCTGCTACA GCCAGGAAGG
 651 GGACTGGGCT GGGGTGGGAA CCACAGGTAG GCATCGGAGG GGCTGCCAGT
 701 AGACCTGGTT TGGGTGGCGC TGCCGGTAGA GCTGGTTGGG GCGGGGCTGC
 751 AGGTGGAGCT GGTTGGGCG GGGCTGCAGG TGGAGGTGGT TGGGCGGGG
 801 CTGCAGGTGG AGATGGTTGG GGCGGGGCTG CAGGTGGAGG TGGTTGGGGC
 851 GGGGCTGCAG GTGGAGGCGG TTGAGGGGAG CAAGGTGGGA GGTGGAGCAG
 901 CTGCTATTTA AGAGGGGTG GTGGTGCCGG TTCTGCAATT AGGTTACTGT
 951 GTCTTGCTGG GGCTTGGTCT TGTTTGCTGA AGGGGCAGCA GGGCTCTACC
1001 ATGGAGGGTG TAGGGGGTCT CTGGCCTTGG GTGCTGGGTC TGCTCTCCTT
1051 GCCAGGTAAG CTGGCTGCCT GTCCCTCCTG CTGCTGGCTC CAGCCTGGAG
1101 AAAGCTGGGG AGAGGCTAGA AGGTTGTGGC TGGAGCCTGC AGGGATTGTA
1151 GCTGAGCTCA GTAGCTCAGA GCACAGAGCT CTCCAGGGTT ATTCTAGAAG
1201 TCAGCTCCTG GGGGGCCAAG GGGAGGCCTC CTGAAGGCCC TGGAAGCAGA
1251 GGGCCTGCCT GGCAGAAGAT AAGTGTTGTG CCCCAGGCCT ACTTGTCTTG
1301 GGGTGGGGGT AGGCTGTAAG TCCCCACTCC AGCCTGGTCA GGCAGGGAGT
1351 CATCCAGGCT GAGCCCATTG TCCAAGAGCC TGGGCTGAGA GAGAGTCATA
1401 AGGTGGGGTC TGAGGCTGGC CCTGCCCGTC ACGGGCGTCA GAACCCGAGG
1451 TCTGTCCTGC CTCCTTCCTT CCTGCCCCTC CTCTACCTCA TAGGTGGGGC
1501 ACATGGTCCC TTTTGGTCCC CCTAAGGGAG CTCCTTCCCT GAGGTCATCT
1551 AGACCTTGGC ACCAGTTGGG GTTGAGCAGG GAGGCTGGGA AGGCTCCTTG
1601 GCTTTGTGCT GGAGCCTACT CTTCCTAGGG ACTGAGTCTT ACCGTCTGAT
1651 CCCCCACACC CACCCCATGT CCTGCTGTCT GGTCTCACCG GTGGGTGCTC
1701 CAGGCATCTG TGTATGCCCC TGTCTGTCTG GACCAGGTGT GATCCTAGGA
1751 GCGCCCCTGG CCTCCAGCTG CGCAGGAGCC TGTGGTACCA GCTTCCCAGA
1801 TGGCCTCACC CCTGAGGGAA CCCAGGCCTC CGGGGACAAG GACATTCCTG
1851 CAATTAACCA AGGTGAGGGC ACTACATCTT CTCACGGCCT GGAGGGGCAC
1901 GACGTTATGT AGTGTGAAAA CCACACCGAA CACTCAGAAA TGCAGAGCCT
1951 GGGAGGAAAT GGACCAGCTT ACTCTGGGCT CTAAGTGGTT TTTAAGAGAT
2001 GGAGTGGTGT TGCTATATTG CCCCGGCTGG TCTTGAACTC CTGGCCTTAA
2051 GTGATCTTCC TGCCTCTGCC TCCCGAGCAG CTGGGACTAC AGGTGTGAAT
2101 GGGTGGAAAT TCTATGGGCA ATTGCTTAAG TCTACTCTTT CTTTTTGTAT
2151 CTTTCTTAGT GGATTGTTAC TTTTATAAGA AAACCAAGC TCTTAAAGGG
2201 CCTGGGCGTG GAGCTAAGCG GTTAGTCGCA GTCTGAGATT GTCAGCCACC
2251 CTGTGCAGGA CTGTCTGCAG GTGTGATTAA GAAGTCTGAA GCTCAGCTGG
2301 GTGCGGTGGC TCTCGCCTGT AGTCCCAGCA CTTTGGGAGG CTGAGGCGGG
2351 CAGATCATGA GGTCAGGAGA TCGAGACCAT CCTGGCTAAC ACAGTGAAAC
2401 CCCGTCCCCA CCAAAAATAC AAAAATTAGC CGGGCGTGGT GGCGGGCGCC
2451 TGTAGTCCCA GCTACTCAGG AGGCTGAGGC AGGAGAATGG CATGAACCTG
2501 GGAGGCGGAG CTTGCAGTGA GCTGAGATTG CGCCACTGCA CTCCAGCCTG
2551 GGCGACAGAG CATCTCACAA AAAACAAAAA ACAAAAGTCA GGCTCAGGGC
2601 CTTGCTGTCT GGGGATGTCA GCTGAGGAAT GAGGGTGTAT AAATAGCCTG
2651 AACAAAGCCA GTTGAAATGG AGACTGGAGT TCAGATGTTG GAGCAATGAG
2701 GGCTGAAGCA CTCAGGGTTG AAGCAATCGG GCTGAACAGG GACAACCTT
2751 GCCCTAAGGG TGGGTGAGAT CCTACCAGAT GTGGTAGCCA CTGTGTGATC
2801 TGCCCCCTTC TTCCTCTGTG AGCTGACTTG GGAGCCCAGC GCCAGCTGAG
2851 CCTTGAGCCC CAGGCACCAT CCCACCCCTG GATCACCGTG AGTGGTCTGC
2901 AGGTAACCAG AACCAATGGA GAAAACTCCC AAATGCTGGT GACCCCAACA
2951 ACTATCCTAT CACCTACGGT GAGGCTGTCT CATAAGGGCT GCCCGTGCCT
```

FIGURE 3A

```
3001  TACCCAGTGC  TTTCCTGGGA  AGCACCTGCC  CATCTCCAGC  CACTGTGAAT
3051  ATGGCTAATG  CTGCACAGCT  GTCTGCCTCC  CAAAACTGGC  CCTTGGCCAG
3101  AAGGAGCTGC  CTCAGCCAGA  GATGCCCGGG  GGCTACTCCC  TTGTCTGCCC
3151  AAGGTGGCCT  ACTGTGACTT  CTAAGGGACA  GGAGTCTGGC  TCCTGCCTAA
3201  AGGTGGTACA  AGTCAGCGGT  GTCATTTGTG  GTCTGGAGCG  CCCATGGGAT
3251  CTGGCTGAGG  CTGTGCCTGG  GTTCTTCCCT  GCCTTCTCTC  CTGCTTCCCT
3301  CACTCCCCCT  GTGAGTCACT  TGTGGGAGAC  CCGGCTCAGG  GAGAGATGAG
3351  AAGCAGAGGG  ACTAAGAGGG  GAGAGGGGCT  TGCGAGAGCC  GGTATTTGCC
3401  TGCCTCTGAT  GGTGGAACAA  ATTTGTGGAA  CAAAATTGCC  ACCTCAAGGG
3451  GCCTGAATAT  AACAGATGGG  TGGGAATAG   ATGGGGGATG  AGGTGGGCAG
3501  GAGACCCCAG  GGCCTGTTCT  GAGGAGTGTG  GCTCAGGCTG  GAAGAAGCCA
3551  CTGCTTCCTG  ACAGCAGGGA  CCCGGGCTTG  GGACTGGATT  GCGTGGGTCA
3601  TGGGCTGTGT  TTGAGCAGGG  GAAGGCTGCA  GTCCAGCCGA  GAAGCCTTGC
3651  ACACTCAGGG  ACTGTGTGAC  TTCCCTGAGG  CCACGCAGGC  TCAGTGCTCA
3701  GGGAACCTCT  AGCTCCACAG  TCAGGAGAGG  GACAGACCCC  AAGCCTCAGT
3751  CTCCTTTGTC  TTTGTCCTCC  AGCCCCCTCA  CACCTGCAGA  CAGTCCGCAC
3801  AGGGTGGCTG  ACATTCTCAA  ACATCAACTA  ATGACTTAAC  TAAACACCCA
3851  GGCTCGGAGA  GCCGATGACC  TATACTTTTA  TCAGGCTATT  TAAGAACTTA
3901  TAAAAGTAAC  AATCCACTAG  GAAAGACACA  AGAATAGACT  TAAGTAAGTA
3951  GGGATTTGCT  TGGCCTGTCC  CACGAGTCAG  TGTTCTGGGG  GACATGGGCC
4001  AACACGTCCT  TCTTCCTTTC  CCAGGGCTCA  TCCTGGAAGA  AACCCCAGAG
4051  AGCAGCTTCC  TCATCGAGGG  GGACATCATC  CGGCCGGTGA  GTGCACACAC
4101  TGACGTGTGT  GGGTGCGGAT  AAGCCCACAG  TTGGCGACAG  GTCCTCTGAG
4151  CCCACCCTGG  ATGCCATGGG  GCCTGATGTG  TGAGGGACAT  ACATAGCTTG
4201  GTAGATGCCT  CTTTTTGTCA  AGGTCAGAGC  GACTGTTCTG  TTAGGAAATA
4251  GGAATAAGCC  AGCCTGAATG  CTAAGGAAGG  CTGGTATCTG  AAGTGCTGGC
4301  ACAGTCAGCC  TGAGAGGGCT  TCCTGAAGGA  GGAGGTTTGA  ACACTTGACC
4351  CAGCTTGGTA  CCCTGCCCAG  GGGAGGTGCT  CAGCACTCGG  GAGGTGCTCA
4401  GATAAAGGAA  GAGATGAGCA  AGGGTTGGCA  GAGTGGCCAG  TGGCAGATAA
4451  AGGGCCTGGT  GGCAGTGGCG  ACCTAGGGAT  GGTGGAACAA  GGAGTGATGT
4501  TGAGCCTGAC  CATCTTGGCT  GTGGTCGAGG  GGCCGCATCT  GAAGGGAGAA
4551  GGTTGCTGGG  GATTGGGGCG  CCTTGCTAAC  AGAAAAGGGA  ACACTGTGCC
4601  CAGGATGGCA  GCCATGTGTT  TCAGGCAACT  GCGAATGGCA  GAAGGCTCCT
4651  GAATAGGACA  GTGACCCAGG  GGAAGGCAAG  ACTGTCCTGT  TGGAGGCTGC
4701  CACTGACGGC  ACAGCCTCTG  GCTGGGCAGG  AGAGCCAGAG  GCTGGCCCAA
4751  GGCTGCCCAG  GAACTCCGGG  GGCAGGGCAG  ACCCTCTGGG  TTATGCAGTG
4801  AGTGCTCGGG  CAGGTGGTGT  GCGACCACCC  GGAGCAGAAT  CAAATGCCTC
4851  CAGCCGATGG  CACAGGCACG  CTGGGGTGCT  GTGGAGCCTG  GGCACCGAAG
4901  GGCTCTGGTT  GCTGGAGAGC  AGAAGTAAGC  AGCCGAGGCC  AGGGTGCTGC
4951  CTCACTTTCA  CTCCATATGG  CTCTGTTCCC  ATGATCGTCC  CATGTTCAGG
5001  GAAGCCTGGT  GGCTGTTCCC  CTCTGGAAGG  GGCACTGTCA  ACATGCTGGA
5051  GTGGGCTGC   TGGCCCAAGC  CCTTCTGATT  CAGGGCACCC  TGGGGTGCTG
5101  GGCCTCCTAG  CCAACATCCT  CAGGGACTAA  TCTCTTGTTT  GCTTGAGATT
5151  GAAATTCTTT  CATCATAGGC  CAAGGGACTG  TCTTGTGCAT  CAAGGTTCAT
5201  GTAGCTGGCC  CCTTGCCTTC  CACAGCTCTG  TCCCATCTCT  AATGGTCCCC
5251  CATTCCCATG  CACACAGGTC  CTGACTCCCA  CATCTTTGGG  GTTCTGGTGC
5301  CCTGGGGTGT  GGTACCCTTG  GGCACAAAG   CTTGGGTGGC  CTCTGTCCCC
5351  AGGGGTTGAA  CTGCTGCTCT  CTCCTCAGAG  TCCCTTCCGA  CTGCTGTCAG
5401  CAACCAGCAA  CAAATGGCCC  ATGGGTGGTA  GTGGTGTCGT  GGAGGTCCCC
5451  TTCCTGCTCT  CCAGCAAGTA  CGGTGAGTGA  GCATGGCGCG  CTCCCTCCCT
5501  GCCTCAGCCC  CTTCTTCCTA  ATGCGGCAGG  TGTTCCTCTC  TTCCCTTTTC
5551  CTCTTACACC  ATCACATCCC  TTCCACCTCC  CCACCCGAAG  AACCTGTCCA
5601  CAGATGCCCT  TCTGTTGCTG  AAGGTCTCCT  GAGTAGGGAG  GGTTAAAATC
5651  TGATGGGAAG  GTATGTCGAG  TGGGGATCTG  GTTCCCCTTG  AGACCATGCG
5701  GTGCAGAGGA  CAGTGACCTA  CCCAAGGCCA  CACAGCCAGG  GTCTGTCTGG
5751  GGCCCAGCTT  CTTCCTGGCA  CCACTAAGCT  GCCCTTTCTT  GATGCTATTT
5801  TGGGAGAGTG  AGTTCAGAGC  TCTGCTCCCA  GACCCTCAGG  TAGAGCTCAA
5851  AGACCACCAG  GGCTCTGGGG  GCTCAGCCAG  GTGGTGTCTT  CCAGATGAGC
5901  CCAGCCGCCA  GGTCATCCTG  GAGGCTCTTG  CGGAGTTTGA  ACGTTCCACG
5951  TGCATCAGGT  TTGTCACCTA  TCAGGACCAG  AGAGACTTCA  TTTCCATCAT
```

FIGURE 3B

```
6001  CCCCATGTAT GGGTAAGTGC CGGGGCCAGG ATGCGTATCT CAGCTCGCTT
6051  CTGCGTTCAG CCCGGAATTA ACTTGGCCAT TGTCTAAAAT GTATTCCTGG
6101  GCCCATCCTC CAGGGCTCAG TCTCCCTGCC CACCCTGAGG GGTCTGCCAA
6151  GTGTGAGCTG GACCTCCAGG GCGGAATGTG GGAAAGGGAT GGGAACGGTG
6201  CTAGACCCTC CATTTACAAA GCCCTCCTCT CCCGGGGGAC TCCATGAGGT
6251  GGTGAGGAGA GGAGGTTTTG CGGGGCAGAC AGTGCGTGAG TCACTGAGTC
6301  CTGGCAAGTC CCCTAACTTC TGAGCCTCTT CTGTCCCCTC TGGGGTGCGA
6351  GTGGTGGCGA TACCTGCTTC CTAGCTTGTC AGGGGCCTGA GGCAATTTGT
6401  GTGAAAGCCT TGGCTTAGGG CTGACCAGGA GGGTGTGCTC ACTTAGTAAG
6451  CTGCTTCTGT CCTCTGTGTT CATATATCAG TTTCTGCAGC CTCCCTGCAG
6501  CCCAGGCTGG TGATGGGGGT CCGGTATGGC CATTTCACAG AAGTCCAGGC
6551  AGTAAAGGGG CCTGGAGAAT GGTGAACCTG AGACTAGAGC CCAGAGTGGG
6601  GCCTGCCTGT TGGGAGTTTG TCTATCTTGT GTTGTGTGGG GAGGGAGAGC
6651  CCAGGTCTGT ATGTCCGGAG GGATCTGGGC TGGCACTTAC CCCACTTGCT
6701  CTCATCACCC TGCAGGTGCT TCTCGAGTGT GGGGCGCAGT GGAGGGATGC
6751  AGGTGGTCTC CCTGGCGCCC ACGTGTCTCC AGAAGGGCCG GGGCATTGTC
6801  CTTCATGAGC TCATGCATGT GCTGGGCTTC TGGCACGAGC ACACGCGGGC
6851  CGACCGGGAC CGCTATATCC GTGTCAACTG GAACGAGATC CTGCCAGGTG
6901  AGCCAGGCCA CACGCAGGAC AGGCTGGTGC CGGGGAGGGG ACAGCACGGC
6951  TTGGGCCCAA GTCGCCTGGT CCCCATGGGT GAGGCTATCC ATCCTCCCCA
7001  TCACCTGCCT GCTTCCTGTG GGAAGGTGG GGGTCTCACT TCTGTCTGGT
7051  ACCTGGTACC TGGAGGTGGT ACTCTGGGTG CTGCTCTGGG CCCCAGGCCT
7101  TCCTCTACCC ACCTGTAGTT GTGCCTTAGC TAGGGCGCCA CCACCTGCTT
7151  TGTCTCGCTT CTCATCCCTG ACACTGTCCT CTCCCTGGCG ATGGGGCAGG
7201  CAGTGCCCAT GATACCTGCT TGTTGAGTAC TCTAGCAGCG GTCTCATGTA
7251  CCAGATACCA CCACCATGGA CTGGGGCTGT GTGCCAGCTT GGGGAGCTGA
7301  GCCAAAGTGG GACCCCAAGG TAGCAGGCTG CACAAGCCAA GTGCTGGGCC
7351  ACGGGCTGAG GGCAGCACTG TGGGGCTGGG ACATGTGCCA GTGGTGCCAG
7401  TGAGCAGGCA GAAGGAACAC AGACTGTGGC CATGGGAGAG TGGAGGCTGG
7451  AGGCAGGTGG GCTGTGGTTC CTGTGCTGGC AGCGGCTGTG TGGCGCCGGG
7501  GATCAGATCC TGGTGATGGT GGGGTCTCTC TCATTGTGGG CTTGATGGTC
7551  TGGTTCAGGA GGCAGGAAGA GCCCCACGAG GGAGGGGCAG AGGAGGTTTG
7601  GGTGGGAGTC TGGCTTAGGG GTTGGAGCAG GAAGGCCTAC CGCAGGTGGA
7651  GGGCGTCCAG CACGAGACCT TTCAGGGCTG TCATGTTAGC CAGGTGAGGC
7701  AGCCAGGGAA GCTGCCTGGG CCCAAGGACC TTCCCAGGCC CCAAACACCG
7751  CTTTCTCAGT GGCTCTCAGC AAACATGAGT CACAGAGAAA GGGGTGACGG
7801  GGCACGTGGG TAGCACCTCA CAAAGGGGGA GGGGATGGAT ATTGAATCAG
7851  ACCAGGCTGG GGAGGTTGTG AGGGGGGTGA CAAGTGACTC TGTACCCTGA
7901  AAACAGACTG ATCCTTCCCA ATGCTCGTGG AACAGTTGTG AAAGTTTACC
7951  CTGATAATTT TATGATATAC CATGAAATGC CATGAAAACC TGCAACTCTG
8001  AAAGTAGACC AATGTAAACA TTCTGATCAT GATATAAAGT AGAAACCGAT
8051  ACATCAAAAC CGAAAGCTTC TCCTATTCAG AAATTGAAAA AAACAACAAA
8101  ACTTTCTTTC AGCTCTGGAG TTAAAGTACA GCAATTCTAA AAAAAAATCA
8151  TGAAAGACTA GAAAAGCCAA TGGTTCACAG CTAAAGCAAT GCTCAGAGAA
8201  AATGTGTAGA CTTACGTATC AGTAAACAGA ACAAATTGAG CATGTCAACC
8251  CAAGTTAAAT GAAAGCAGGA GGGAATTTCA AAAGGTAAAA GCAGAAATTG
8301  AGTTGGAAAA CAGCACTAAT AATTATTCCT AATGATAAAA CAGGCTAAAA
8351  CACGGGTTCC CCAGTGGAAA AAATGAGAAC ATATTTGTTC CCATTTAGGT
8401  TAATATGTTC TCATTAGGTT AACATGTACA GAAACTGCCA GGGCAGACAC
8451  ATTAATAACA GTAATTAACT GTTGTGGGGC GGGGAGGTGG GAACTCAGGA
8501  AGCAGGGGAT GGAATAGACT TTTACTACAT CTCAATATTT GACTTTTGAA
8551  CCAAATGAAT ATACTACTTA TTCAAAAGTA TGTTTAATGA ATTTTTAAAA
8601  AGAAGTAAGA GCTCAAGAGG CAGCTATGTT AGGCAGGTGG TGGGGTATGA
8651  AGGTGCTGGA GGGCTCATTT GCTCCATGGA GAGGAAGCTG CTGTGACCGA
8701  GGTGGCGTGT ATGCGTGGCT GGCTGGCTGG ATTTGGGAGG ATTGGGGGAG
8751  CAATCCCTCT GAAGGCCTGG GGGACTTGAG TGAGGGGAG ATGGGCTCCA
8801  AATCTGGGGA AGTGTTGTGG CCTGACACAG GAAGAACAGG TGGGCCTGTG
8851  ACTGGGGACT AGGGCATCAC CACTGCAGAT GACAGCGTGG CAGCTTTTTA
8901  AAGCTGGGTC AAGGAATAGA CATTTCATCT GGGGTGGGAG GGACATCTGA
8951  GACCCTGAGC AGTGTGGGAC CCGTGGCAGC TGTGGCTTAT GCAGAGACCA
```

FIGURE 3C

```
 9001  GCCCCGTGCA GACTGAATAT GCAAGGAGGA AGGATGGGTG GAGGGAACAG
 9051  CTAGGAGGTG ATGGTTGGCC AGCCATGGGG TCCCTGTGCC TCTACCTCAA
 9101  CTAGTACAGG TTGGGGATCC TCCCAGGGCT GGGAAAGTGG GACTGGTACC
 9151  AGAAGCAGCA TGGTGGCTGT GGGCTCAGCC CCTCAGCTTG GGTGAGTTAT
 9201  GAGCTCCCAG AAGACTCTCC CAGCCATTGC CTGCCCTTTC TTGCCTGCCC
 9251  TCTTTATATA TCAGTAAGTT GTATTGTTTT TGTATTTTTA GGCTTTGAAA
 9301  TCAACTTCAT CAAGTCTCGG AGCAGCAACA TGCTGACGCC CTATGACTAC
 9351  TCCTCTGTGA TGCACTATGG GAGGTGAGGA CCCTGCCTTC TTCTCCCTCT
 9401  GCTTCCCCCA GCCTCTCCCG TGGTGATCTG GACTCAGGGG TCTCCCGCTG
 9451  GGTTCCAGGC TCGCCTTCAG CCGGCGTGGG CTGCCCACCA TCACACCACT
 9501  TTGGGCCCCC AGTGTCCACA TCGGCCAGCG ATGGAACCTG AGTGCCTCGG
 9551  ACATCACCCG GGTCCTCAAA CTCTACGGCT GCAGCCCAAG TGGCCCCAGG
 9601  CCCCGTGGGA GAGGTGAGTG GCATGGCAGG AAGGTGACTT GAACCTGGAG
 9651  AAGGCGCCTG TGCTCTAATG GTGTCAGGGA GGGTGACAAG GAGGGAGATG
 9701  AGGTTGCAGG GGGAGCAGGG TGAGATCACG GGGGCTTGCC ACAACGACGC
 9751  AGAACAAGCA CTTGAGGAAA GTTAACACTC ACTATGACTC AACTGTAACC
 9801  AAAGAGGAAT AGGGCTCACT TGCTTAGCCT AGATAATAAA CATCTACCAA
 9851  AAACCTAGAA CAAAAGTTAA GGGTAAAACA TTAAAACTGG GACCAAGACA
 9901  AGTTTTCCCA CCATTGTCCC ATCTACTCCA CATTGTGTGG CAGTGGAGGT
 9951  CCTGGGCACC GAGGTAGAGC CAAAGAAACT AAAGGTCCGA GGATTGGAAA
10001  GGAAGCAAAA AAATCGTTCA TAATAGATGA TTACCTGTAT TGAAAGCAAC
10051  AATCTATAAA CAAGTTATTA GAACTAATAA GAATTAGAAA AGGTAAATAC
10101  AGTTAATATA AAAATCATAT TTCTGTACAC CCAGTTAGAA AACACAATTG
10151  TTAGTAAACA TACCATTATA ATAGCAATCA TAAAGGTCCC AAGGAATAAA
10201  TCTGACAGCT GTATCAAACA TTTGAGGAAA AATGAACCTT TATTAAAATC
10251  GTTAAATAAT ACTTAAATAT AGATAAATCT GTTATTGAAA GGAAGGCAAT
10301  GTTATAAAAA TTCAGTCTTC CCAAATTAAT CTATAAATTC CCACTCAAAA
10351  TAAGTTTGAT CTTGACAGAG TGATTTTTTT TTTCTTTTTT TTTTTTAAAG
10401  ATGGAGTCTC ACTCTGTCAC CCAGGCTGGA GTGCAGTGGC ACAATCTCGG
10451  CTCACTGCAG TCTCTGCCTC CGAGGTTCAA GTGATTCTTG TGCCTCAATC
10501  TCCTGAGCAG CTGGGCTTAC AGGTGCGTGC CACCACACCC AACTAATTTT
10551  TGTATTTTTA GTGGGACAG GGTTTCACCA TGTTGGCCAG GCTGGTCTTG
10601  AACTCCTGAC CGCAAGTGAT GCGCCTGCCT TGGCCTCCCG AT
```

FEATURES:

| | |
|---|---|
| Start: | 1001 |
| Exon: | 1001-1055 |
| Intron: | 1056-1736 |
| Exon: | 1737-1862 |
| Intron: | 1863-4024 |
| Exon: | 4025-4086 |
| Intron: | 4087-5378 |
| Exon: | 5379-5472 |
| Intron: | 5473-5894 |
| Exon: | 5895-6012 |
| Intron: | 6013-6715 |
| Exon: | 6716-6897 |
| Intron: | 6898-9291 |
| Exon: | 9292-9373 |
| Intron: | 9374-9458 |
| Exon: | 9459-9642 |
| Stop: | 9640 |

FIGURE 3D

SEQUENCE LISTING

<160> NUMBER OF SEQ ID NOS: 4

<210> SEQ ID NO 1
<211> LENGTH: 903
<212> TYPE: DNA
<213> ORGANISM: HUMAN

<400> SEQUENCE: 1

```
atggaggtg tagggggtct ctggccttgg gtgctgggtc tgctctcctt gccaggtgtg     60
atcctaggag cgcccctggc ctccagctgc gcaggagcct gtggtaccag cttcccagat    120
ggcctcaccc ctgagggaac ccaggcctcc ggggacaagg acattcctgc aattaaccaa    180
gggctcatcc tggaagaaac cccagagagc agcttcctca tcgaggggga catcatccgg    240
ccgagtccct tccgactgct gtcagcaacc agcaacaaat ggcccatggg tggtagtggt    300
gtcgtggagg tccccttcct gctctccagc aagtacgatg agcccagccg ccaggtcatc    360
ctggaggctc ttgcggagtt tgaacgttcc acgtgcatca ggtttgtcac ctatcaggac    420
cagagagact tcatttccat catccccatg tatgggtgct tctcgagtgt ggggcgcagt    480
ggagggatgc aggtggtctc cctggcgccc acgtgtctcc agaagggccg gggcattgtc    540
cttcatgagc tcatgcatgt gctgggcttc tggcacgagc acacgcgggc cgaccgggac    600
cgctatatcc gtgtcaactg gaacgagatc ctgccaggct ttgaaatcaa cttcatcaag    660
tctcggagca gcaacatgct gacgccctat gactactcct ctgtgatgca ctatgggagg    720
ctcgccttca gccggcgtgg gctgcccacc atcacaccac tttgggcccc cagtgtccac    780
atcggccagc gatggaacct gagtgcctcg gacatcaccc gggtcctcaa actctacggc    840
tgcagcccaa gtggccccag gccccgtggg agaggtgagt ggcatggcag gaaggtgact    900
tga                                                                  903
```

<210> SEQ ID NO 2
<211> LENGTH: 300
<212> TYPE: PRT
<213> ORGANISM: HUMAN

<400> SEQUENCE: 2

Met Glu Gly Val Gly Gly Leu Trp Pro Trp Val Leu Gly Leu Leu Ser

```
              1               5              10              15
Leu Pro Gly Val Ile Leu Gly Ala Pro Leu Ala Ser Ser Cys Ala Gly
             20              25              30

Ala Cys Gly Thr Ser Phe Pro Asp Gly Leu Thr Pro Glu Gly Thr Gln
             35              40              45

Ala Ser Gly Asp Lys Asp Ile Pro Ala Ile Asn Gln Gly Leu Ile Leu
             50              55              60

Glu Glu Thr Pro Glu Ser Ser Phe Leu Ile Glu Gly Asp Ile Ile Arg
 65              70              75              80

Pro Ser Pro Phe Arg Leu Leu Ser Ala Thr Ser Asn Lys Trp Pro Met
                 85              90              95

Gly Gly Ser Gly Val Val Glu Val Pro Phe Leu Leu Ser Ser Lys Tyr
                100             105             110

Asp Glu Pro Ser Arg Gln Val Ile Leu Glu Ala Leu Ala Glu Phe Glu
                115             120             125

Arg Ser Thr Cys Ile Arg Phe Val Thr Tyr Gln Asp Gln Arg Asp Phe
                130             135             140

Ile Ser Ile Ile Pro Met Tyr Gly Cys Phe Ser Ser Val Gly Arg Ser
145             150             155             160

Gly Gly Met Gln Val Val Ser Leu Ala Pro Thr Cys Leu Gln Lys Gly
                165             170             175

Arg Gly Ile Val Leu His Glu Leu Met His Val Leu Gly Phe Trp His
                180             185             190

Glu His Thr Arg Ala Asp Arg Asp Arg Tyr Ile Arg Val Asn Trp Asn
                195             200             205

Glu Ile Leu Pro Gly Phe Glu Ile Asn Phe Ile Lys Ser Arg Ser Ser
                210             215             220

Asn Met Leu Thr Pro Tyr Asp Tyr Ser Ser Val Met His Tyr Gly Arg
225             230             235             240

Leu Ala Phe Ser Arg Arg Gly Leu Pro Thr Ile Thr Pro Leu Trp Ala
                245             250             255

Pro Ser Val His Ile Gly Gln Arg Trp Asn Leu Ser Ala Ser Asp Ile
                260             265             270

Thr Arg Val Leu Lys Leu Tyr Gly Cys Ser Pro Ser Gly Pro Arg Pro
                275             280             285

Arg Gly Arg Gly Glu Trp His Gly Arg Lys Val Thr
                290             295             300

<210> SEQ ID NO 3
<211> LENGTH: 10642
<212> TYPE: DNA
<213> ORGANISM: HUMAN

<400> SEQUENCE: 3
ttcccttcac tgggtgcagg tgactgtggg ggtgtcccca aatgctgccc agcgctgaca      60
tgctccgcct ctgggatttc aatccaggtg gggccctgag tgacctggct ctggggctca    120
ggggtatgga ggaggggga tataggtaag gagtttaaat ttccaaatct gtgaaatggg     180
aataaatact gactgatcat gccagctgct gtgggattag gggtggact ccctgcgagg     240 ctctgggcat ctggggttc cacctttccc acatggcagg cttttctaggg tgctgcacac    300 tgttcagttt gtgaaatttc ctggagccct gtgcttgtga tagtgaactt ttctatatgt    360
gtactaaaat aaaagcttgt gaaagtgcag tgacctttc ctccttccgg agatacacgg     420
ggggcgcccc agggtctcag gcagctttcc ccatgtctaa gcacaggccg ggtaggaaa     480
```

-continued

```
gggggtctcc ctcgctggag gaataggtct atacctgggc tggggcctca gctaggcctg      540
gagcaacttt ctgcgatgtt tctctgcccc ctggaggcag gaaggaacct cagaagagcc      600
acactcccaa gcgggcccct cctgtctttc acctgctaca gccaggaagg ggactgggct      660
ggggtgggaa ccacaggtag gcatcggagg ggctgccagt agacctggtt tgggtggcgc      720
tgccggtaga gctggttggg gcggggctgc aggtggagct ggttggggcg gggctgcagg      780
tggaggtggt tggggcgggg ctgcaggtgg agatggttgg ggcggggctg caggtggagg      840
tggttggggc ggggctgcag gtggaggcgg ttgaggggag caaggtggga ggtgagcag      900 ctgctattta agagggggtg gtggtgccgg ttctgcaatt aggttactgt gtcttgctgg      960
ggcttggtct tgtttgctga aggggcagca gggctctacc atggaggtg taggggtct      1020 ctggccttgg gtgctgggtc tgctctcctt gccaggtaag ctggctgcct gtccctcctg      1080
ctgctggctc cagcctggag aaagctgggg agaggctaga aggttgtggc tggagcctgc      1140
agggattgta gctgagctca gtagctcaga gcacagagct ctccagggtt attctagaag      1200
tcagctcctg gggggccaag gggaggcctc ctgaaggccc tggaagcaga gggcctgcct      1260
ggcagaagat aagtgttgtg ccccaggcct acttgtcttg ggtgggggt aggctgtaag      1320 tccccactcc agcctggtca ggcagggagt catccaggct gagcccattg tccaagagcc      1380
tgggctgaga gagagtcata agtgggggtc tgaggctggc cctgcccgtc acgggcgtca      1440
gaacccgagg tctgtcctgc ctccttcctt cctgcccctc ctctacctca taggtggggc      1500
acatggtccc ttttggtccc cctaaggag ctccttccct gaggtcatct agaccttggc      1560
accagttggg gttgagcagg gaggctggga aggctccttg gctttgtgct ggagcctact      1620
cttcctaggg actgagtctt accgtctgat cccccacacc cacccatgt cctgctgtct      1680 ggtctcaccg gtgggtgctc caggcatctg tgtatgcccc tgtctgtctg gaccaggtgt      1740
gatcctagga gcgcccctgg cctccagctg cgcaggagcc tgtggtacca gcttcccaga      1800
tggcctcacc cctgagggaa cccaggcctc cggggacaag gacattcctg caattaacca      1860
aggtgagggc actacatctt ctcacggcct ggaggggcac gacgttatgt agtgtgaaaa      1920
ccacaccgaa cactcagaaa tgcagagcct gggaggaaat ggaccagctt actctgggct      1980
ctaagtggtt tttaagagat gggtggtgt tgctatattg ccccggctgg tcttgaactc      2040
ctggccttaa gtgatcttcc tgcctctgcc tcccgagcag ctgggactac aggtgtgaat      2100
gggtggaaat tctatgggca attgcttaag tctactcttt cttttttgtat ctttcttagt      2160 ggattgttac ttttataaga aaaaccaagc tcttaaaggg cctgggcgtg gagctaagcg      2220
gttagtcgca gtctgagatt gtcagccacc ctgtgcagga ctgtctgcag gtgtgattaa      2280
gaagtctgaa gctcagctgg gtgcggtggc tctcgcctgt agtcccagca ctttgggagg      2340
ctgaggcggg cagatcatga ggtcaggaga tcgagaccat cctggctaac acagtgaaac      2400
cccgtcccca ccaaaaatac aaaaattagc cgggcgtggt ggcgggcgcc tgtagtccca      2460
gctactcagg aggctgaggc aggagaatgg catgaacctg ggaggcggag cttgcagtga      2520
gctgagattg cgccactgca ctccagcctg ggcgacagag catctcacaa aaacaaaaa      2580 acaaaagtca ggctcagggc cttgctgtct ggggatgtca gctgaggaat gagggtgtat      2640
aaatagcctg aacaaagcca gttgaaatgg agactggagt tcagatgttg gagcaatgag      2700
ggctgaagca ctcaggggttg aagcaatcgg gctgaacagg ggacaacctt gccctaaggg      2760
tgggtgagat cctaccagat gtggtagcca ctgtgtgatc tgccccttc ttcctctgtg      2820
```

```
agctgacttg ggagcccagc gccagctgag ccttgagccc caggcaccat cccaccoctg    2880 gatcaccgtg agtggtctgc aggtaaccag aaccaatgga gaaaactccc aaatgctggt    2940
gaccccaaca actatcctat cacctacggt gaggctgtct cataagggct gcccgtgcct    3000
tacccagtgc tttcctggga agcacctgcc catctccagc cactgtgaat atggctaatg    3060
ctgcacagct gtctgcctcc caaaactggc ccttggccag aaggagctgc ctcagccaga    3120
gatgcccggg ggctactccc ttgtctgccc aaggtggcct actgtgactt ctaagggaca    3180
ggagtctggc tcctgcctaa aggtggtaca agtcagcggt gtcatttgtg gtctggagcg    3240
cccatgggat ctggctgagg ctgtgcctgg gttcttccct gccttctctc ctgcttccct    3300 cactcccoct gtgagtcact tgtgggagac ccggctcagg gagagatgag aagcagaggg    3360
actaagaggg gagaggggct gcgagagcc ggtatttgcc tgcctctgat ggtggaacaa    3420
atttgtggaa caaaattgcc acctcaaggg gcctgaatat aacagatggg tggggaatag    3480 atggggatg aggtgggcag gagacccag ggcctgttct gaggagtgtg gctcaggctg    3540
gaagaagcca ctgcttcctg acagcaggga cccgggcttg ggactggatt gcgtgggtca    3600
tgggctgtgt ttgagcaggg gaaggctgca gtccagccga aagccttgc acactcaggg    3660 actgtgtgac ttccctgagg ccacgcaggc tcagtgctca gggaacctct agctccacag    3720
tcaggagagg gacagacccc aagcctcagt ctcctttgtc tttgtcctcc agccccctca    3780
cacctgcaga cagtccgcac agggtggctg acattctcaa acatcaacta atgacttaac    3840
taaacaccca ggctcggaga gccgatgacc tatacttta tcaggctatt taagaactta    3900
taaaagtaac aatccactag gaaagacaca agaatagact taagtaagta gggatttgct    3960
tggcctgtcc cacgagtcag tgttctgggg gacatgggcc aacacgtcct tcttcctttc    4020
ccagggctca tcctggaaga aaccccagag agcagcttcc tcatcgaggg ggacatcatc    4080
cggccggtga gtgcacacac tgacgtgtgt gggtgcggat aagcccacag ttggcgacag    4140
gtcctctgag cccaccctgg atgccatggg gcctgatgtg tgagggacat acatagcttg    4200
gtagatgcct cttttttgtca aggtcagagc gactgttctg ttaggaaata ggaataagcc    4260
agcctgaatg ctaaggaagg ctggtatctg aagtgctggc acagtcagcc tgagagggct    4320
tcctgaagga ggaggtttga acacttgacc cagcttggta ccctgcccag gggaggtgct    4380
cagcactcgg gaggtgctca gataaaggaa gagatgagca agggttggca gagtggccag    4440
tggcagataa agggcctggt ggcagtggcg acctagggat ggtggaacaa ggagtgatgt    4500
tgagcctgac catcttggct gtggtcgagg ggccgcatct gaagggagaa ggttgctggg    4560
gattggggcg ccttgctaac agaaaaggga acactgtgcc caggatggca gccatgtgtt    4620
tcaggcaact gcgaatggca gaaggctcct gaataggaca gtgacccagg ggaaggcaag    4680
actgtcctgt tggaggctgc cactgacggc acagcctctg gctgggcagg agagccagag    4740
gctggcccaa ggctgcccag gaactccggg ggcagggcag accctctggg ttatgcagtg    4800
agtgctcggg caggtggtgt gcgaccaccc ggagcagaat caaatgcctc cagccgatgg    4860
cacaggcacg ctggggtgct gtggagcctg gcaccgaag ggctctggtt gctggagagc    4920
agaagtaagc agccgaggcc agggtgctgc ctcactttca ctccatatgg ctctgttccc    4980
atgatcgtcc catgttcagg gaagcctggt ggctgttccc ctctggaagg ggcactgtca    5040
acatgctgga gtggggctgc tggcccaagc ccttctgatt cagggcaccc tggggtgctg    5100
ggcctcctag ccaacatcct cagggactaa tctcttgttt gcttgagatt gaaattcttt    5160
catcataggc caagggactg tcttgtgcat caaggttcat gtagctggcc ccttgccttc    5220
```

```
cacagctctg tcccatctct aatggtcccc cattcccatg cacacaggtc ctgactccca    5280
catctttggg gttctggtgc cctggggtgt ggtacccttg gggcacaaag cttgggtggc    5340
ctctgtcccc aggggttgaa ctgctgctct tccctcagag tcccttccga ctgctgtcag    5400
caaccagcaa caaatggccc atgggtggta gtggtgtcgt ggaggtcccc ttcctgctct    5460
ccagcaagta cggtgagtga gcatggcgcg ctccctccct gcctcagccc cttcttccta    5520
atgcggcagg tgttcctctc ttccttttc ctcttacacc atcacatccc ttccacctcc    5580
ccacccgaag aacctgtcca cagatgccct tctgttgctg aaggtctcct gagtagggag    5640
ggttaaaatc tgatgggaag gtatgtcgag tggggatctg gttcccttg agaccatgcg    5700 gtgcagagga cagtgaccta cccaaggcca cacagccagg gtctgtctgg ggcccagctt    5760
cttcctggca ccactaagct gccctttctt gatgctattt tgggagagtg agttcagagc    5820
tctgctccca gaccctcagg tagagctcaa agaccaccag ggctctgggg gctcagccag    5880
gtggtgtctt ccagatgagc ccagccgcca ggtcatcctg gaggctcttg cggagtttga    5940
acgttccacg tgcatcaggt ttgtcaccta tcaggaccag agagacttca tttccatcat    6000
ccccatgtat gggtaagtgc cggggccagg atgcgtatct cagctcgctt ctgcgttcag    6060
cccggaatta acttggccat tgtctaaaat gtattcctgg gcccatcctc cagggctcag    6120
tctccctgcc caccctgagg ggtctgccaa gtgtgagctg acctccagg gcggaatgtg    6180 ggaaagggat gggaacggtg ctagaccctc catttacaaa gccctcctct cccgggggac    6240
tccatgaggt ggtgaggaga ggaggttttg cggggcagac agtgcgtgag tcactgagtc    6300
ctggcaagtc ccctaacttc tgagcctctt ctgtcccctc tggggtgcga gtggtggcga    6360
tacctgcttc ctagcttgtc aggggcctga ggcaatttgt gtgaaagcct tggcttaggg    6420
ctgaccagga gggtgtgctc acttagtaag ctgcttctgt cctctgtgtt catatatcag    6480
tttctgcagc ctccctgcag cccaggctgg tgatgggggt ccggtatggc catttcacag    6540
aagtccaggc agtaaagggg cctggagaat ggtgaacctg agactagagc ccagagtggg    6600
gcctgcctgt tgggagtttg tctatcttgt gttgtgtggg gagggagagc ccaggtctgt    6660
atgtccggag ggatctgggc tggcacttac cccacttgct ctcatcaccc tgcaggtgct    6720
tctcgagtgt ggggcgcagt ggagggatgc aggtggtctc cctggcgccc acgtgtctcc    6780
agaagggccg gggcattgtc cttcatgagc tcatgcatgt gctgggcttc tggcacgagc    6840
acacgcgggc cgaccgggac cgctatatcc gtgtcaactg gaacgagatc ctgccaggtg    6900
agccaggcca cacgcaggac aggctggtgc cggggagggg acagcacggc ttgggcccaa    6960
gtcgcctggt cccatggggt gaggctatcc atcctcccca tcacctgcct gcttcctgtg    7020
gggaaggtgg gggtctcact tctgtctggt acctggtacc tggaggtggt actctgggtg    7080
ctgctctggg cccaggcct tcctctaccc acctgtagtt gtgccttagc tagggcgcca    7140
ccacctgctt tgtctcgctt ctcatccctg acactgtcct ctccctggcg atgggcagg    7200 cagtgcccat gatacctgct tgttgagtac tctagcagcg gtctcatgta ccagatacca    7260
ccaccatgga ctggggctgt gtgccagctt ggggagctga gccaaagtgg gaccccaagg    7320
tagcaggctg cacaagccaa gtgctgggcc acgggctgag ggcagcactg tggggctggg    7380
acatgtgcca gtggtgccag tgagcaggca gaaggaacac agactgtggc catgggagag    7440
tggaggctgg aggcaggtgg gctgtggttc ctgctggc agcggctgtg tggcgccggg    7500
gatcagatcc tggtgatggt ggggtctctc tcattgtggg cttgatggtc tggttcagga    7560
```

```
ggcaggaaga gccccacgag ggaggggcag aggaggtttg ggtgggagtc tggcttaggg        7620
gttggagcag gaaggcctac cgcaggtgga gggcgtccag cacgagacct ttcagggctg        7680
tcatgttagc caggtgaggc agccaggaa gctgcctggg cccaaggacc ttcccaggcc          7740
ccaaacaccg ctttctcagt ggctctcagc aaacatgagt cacagagaaa ggggtgacgg        7800
ggcacgtggg tagcacctca caaaggggga ggggatggat attgaatcag accaggctgg        7860
ggaggttgtg agggggtgta caagtgactc tgtaccctga aaacagactg atccttccca        7920
atgctcgtgg aacagttgtg aaagtttacc ctgataattt tatgatatac catgaaatgc        7980
catgaaaacc tgcaactctg aaagtagacc aatgtaaaca ttctgatcat gatataaagt        8040
agaaaccgat acatcaaaac cgaaagcttc tcctattcag aaattgaaaa aaacaacaaa        8100
actttctttc agctctggag ttaaagtaca gcaattctaa aaaaaaatca tgaaagacta        8160
gaaaagccaa tggttcacag ctaaagcaat gctcagagaa aatgtgtaga cttacgtatc        8220
agtaaacaga acaaattgag catgtcaacc caagttaaat gaaagcagga gggaatttca        8280
aaaggtaaaa gcagaaattg agttggaaaa cagcactaat aattattcct aatgataaaa        8340
caggctaaaa cacgggttcc ccagtggaaa aaatgagaac atatttgttc ccatttaggt        8400
taatatgttc tcattaggtt aacatgtaca gaaactgcca gggcagacac attaataaca        8460
gtaattaact gttgtgggc ggggaggtgg gaactcagga agcaggggat ggaatagact         8520
tttactacat ctcaatattt gacttttgaa ccaaatgaat atactactta ttcaaaagta        8580
tgtttaatga atttttaaaa agaagtaaga gctcaagagg cagctatgtt aggcaggtgg        8640
tggggtatga aggtgctgga gggctcattt gctccatgga gaggaagctg ctgtgaccga        8700
ggtggcgtgt atgcgtggct ggctggctgg atttgggagg attgggggag caatccctct        8760
gaaggcctgg gggacttgag tgaggggag atgggctcca aatctgggga agtgttgtgg         8820
cctgacacag gaagaacagg tgggcctgtg actgggact agggcatcac cactgcagat         8880
gacagcgtgg cagcttttta agctgggtc aaggaataga catttcatct ggggtgggag         8940
ggacatctga gaccctgagc agtgtgggac ccgtggcagc tgtggcttat gcagagacca        9000
gccccgtgca gactgaatat gcaaggagga aggatgggtg gagggaacag ctaggaggtg        9060
atggttggcc agccatgggg tccctgtgcc tctacctcaa ctagtacagg ttggggatcc        9120
tcccagggct gggaaagtgg gactggtacc agaagcagca tggtggctgt gggctcagcc        9180
cctcagcttg ggtgagttat gagctcccag aagactctcc cagccattgc ctgccctttc        9240
ttgcctgccc tctttatata tcagtaagtt gtattgtttt tgtattttta ggctttgaaa        9300
tcaacttcat caagtctcgg agcagcaaca tgctgacgcc ctatgactac tcctctgtga        9360
tgcactatgg gaggtgagga ccctgccttc ttctccctct gcttccccca gcctctcccg        9420
tggtgatctg gactcagggg tctcccgctg ggttccaggc tcgccttcag ccggcgtggg        9480
ctgcccacca tcacaccact ttgggccccc agtgtccaca tcggccagcg atggaacctg        9540
agtgcctcgg acatcacccg ggtcctcaaa ctctacggct gcagcccaag tggccccagg        9600
ccccgtggga gaggtgagtg gcatggcagg aaggtgactt gaacctggag aaggcgcctg        9660
tgctctaatg gtgtcaggga gggtgacaag gagggagatg aggttgcagg gggagcaggg        9720
tgagatcacg ggggcttgcc acaacgacgc agaacaagca cttgaggaaa gttaacactc        9780
actatgactc aactgtaacc aaagaggaat agggctcact tgcttagcct agataataaa        9840
catctaccaa aaacctagaa caaaagttaa gggtaaaaca ttaaaactgg gaccaagaca        9900
agttttccca ccattgtccc atctactcca cattgtgtgg cagtggaggt cctgggcacc        9960
```

-continued

```
gaggtagagc caaagaaact aaaggtccga ggattggaaa ggaagcaaaa aaatcgttca    10020
taatagatga ttacctgtat tgaaagcaac aatctataaa caagttatta gaactaataa    10080
gaattagaaa aggtaaatac agttaatata aaaatcatat ttctgtacac ccagttagaa    10140
aacacaattg ttagtaaaca taccattata atagcaatca taaaggtccc aaggaataaa    10200
tctgacagct gtatcaaaca tttgaggaaa aatgaacctt tattaaaatc gttaaataat    10260
acttaaatat agataaatct gttattgaaa ggaaggcaat gttataaaaa ttcagtcttc    10320
ccaaattaat ctataaattc ccactcaaaa taagtttgat cttgacagag tgatttttt    10380 tttcttttt ttttttaaag atggagtctc actctgtcac ccaggctgga gtgcagtggc    10440
acaatctcgg ctcactgcag tctctgcctc cgaggttcaa gtgattcttg tgcctcaatc    10500
tcctgagcag ctgggcttac aggtgcgtgc caccacaccc aactaatttt tgtattttta    10560
gtggggacag ggtttcacca tgttggccag gctggtcttg aactcctgac cgcaagtgat    10620
gcgcctgcct tggcctcccg at                                             10642
```

<210> SEQ ID NO 4
<211> LENGTH: 268
<212> TYPE: PRT
<213> ORGANISM: HUMAN

<400> SEQUENCE: 4

```
Leu Leu Phe Leu Leu Gly Ile Ala Gln Ala Leu Pro Val Gln Asn Glu
1               5                   10                  15

Glu Gly His Glu Glu Gly Asn Lys Glu Gly His Gly Glu Glu Gly Val
            20                  25                  30

Glu Glu Gly Asp Glu Asp Phe Val Asp Phe Thr Thr Arg Ile Leu
        35                  40                  45

Thr Ser Asn Asn Asn Thr Asp Gln Leu Leu Leu Glu Gly Asp Leu Val
    50                  55                  60

Ala Pro Thr Asn Arg Asn Ala Met Lys Cys Trp Tyr Asn Ser Cys Phe
65                  70                  75                  80

Trp Lys Lys Ala Ser Asn Gly Phe Val Val Ile Pro Tyr Val Ile Ser
                85                  90                  95

Ser Gln Tyr Ser Arg Gly Glu Val Ala Thr Ile Glu Gly Ala Met Arg
            100                 105                 110

Ala Phe Asn Gly Arg Thr Cys Ile Arg Phe Val Arg Arg Thr Asn Glu
        115                 120                 125

Tyr Asp Phe Ile Ser Val Val Ser Lys Asn Gly Cys Tyr Ser Glu Leu
    130                 135                 140

Gly Arg Lys Gly Gly Gln Gln Glu Leu Ser Leu Asn Arg Gly Gly Cys
145                 150                 155                 160

Met Tyr Ser Gly Ile Ile Gln His Glu Leu Asn His Ala Leu Gly Phe
                165                 170                 175

Gln His Glu Gln Thr Arg Ser Asp Arg Asp Ser Tyr Val Arg Ile Asn
            180                 185                 190

Trp Gln Asn Ile Ile Pro Ala Ser Ala Tyr Asn Phe Asn Lys His Asp
        195                 200                 205

Thr Asn Asn Leu Asn Thr Pro Tyr Asp Tyr Ser Ser Ile Met His Tyr
    210                 215                 220

Gly Arg Asp Ala Phe Ser Ile Ala Tyr Gly Arg Asp Ser Ile Thr Pro
225                 230                 235                 240

Ile Pro Asn Pro Asn Val Pro Ile Gly Gln Arg Asn Gly Met Ser Arg
```

```
                    245                 250                 255
Trp Asp Ile Thr Arg Ile Asn Val Leu Tyr Asn Cys
            260                 265
```

ISOLATED HUMAN PROTEASE PROTEINS, NUCLEIC ACID MOLECULES ENCODING HUMAN PROTEASE PROTEINS, AND USES THEREOF

FIELD OF THE INVENTION

The present invention is in the field of protease proteins that are related to the choriolytic hatching protease subfamily, recombinant DNA molecules, and protein production. The present invention specifically provides novel peptides and proteins that effect protein cleavage/processing/turnover and nucleic acid molecules encoding such peptide and protein molecules, all of which are useful in the development of human therapeutics and diagnostic compositions and methods.

BACKGROUND OF THE INVENTION

The proteases may be categorized into families by the different amino acid sequences (generally between 2 and 10 residues) located on either side of the cleavage site of the protease.

The proper functioning of the cell requires careful control of the levels of important structural proteins, enzymes, and regulatory proteins. One of the ways that cells can reduce the steady state level of a particular protein is by proteolytic degradation. Further, one of the ways cells produce functioning proteins is to produce pre or pro-protein precursors that are processed by proteolytic degradation to produce an active moiety. Thus, complex and highly-regulated mechanisms have been evolved to accomplish this degradation.

Proteases regulate many different cell proliferation, differentiation, and signaling processes by regulating protein turnover and processing. Uncontrolled protease activity (either increased or decreased) has been implicated in a variety of disease conditions including inflammation, cancer, arteriosclerosis, and degenerative disorders.

An additional role of intracellular proteolysis is in the stress-response. Cells that are subject to stress such as starvation, heat-shock, chemical insult or mutation respond by increasing the rates of proteolysis. One function of this enhanced proteolysis is to salvage amino acids from non-essential proteins. These amino acids can then be re-utilized in the synthesis of essential proteins or metabolized directly to provide energy. Another function is in the repair of damage caused by the stress. For example, oxidative stress has been shown to damage a variety of proteins and cause them to be rapidly degraded.

The International Union of Biochemistry and Molecular Biology (IUBMB) has recommended to use the term peptidase for the subset of peptide bond hydrolases (Subclass E.C 3.4.). The widely used term protease is synonymous with peptidase. Peptidases comprise two groups of enzymes: the endopeptidases and the exopeptidases, which cleave peptide bonds at points within the protein and remove amino acids sequentially from either N or C-terminus respectively. The term proteinase is also used as a synonym word for endopeptidase and four mechanistic classes of proteinases are recognized by the IUBMB: two of these are described below (also see: *Handbook of Proteolytic Enzymes* by Barrett, Rawlings, and Woessner A P Press, N.Y. 1998). Also, for a review of the various uses of proteases as drug targets, see: Weber M, Emerging treatments for hypertension: potential role for vasopeptidase inhibition; Am J Hypertens 1999 November;12(11 Pt 2):139S–147S; Kentsch M, Otter W, Novel neurohormonal modulators in cardiovascular disorders. The therapeutic potential of endopeptidase inhibitors, Drugs R D 1999 April;1(4):331–8; Scarborough R M, Coagulation factor Xa: the prothrombinase complex as an emerging therapeutic target for small molecule inhibitors, J Enzym Inhib 1998;14(1):15–25; Skotnicki J S, et al., Design and synthetic considerations of matrix metalloproteinase inhibitors, Ann NY Acad Sci 1999 June 30;878:61–72; McKerrow J H, Engel J C, Caffrey C R, Cysteine protease inhibitors as chemotherapy for parasitic infections, Bioorg Med Chem 1999 April;7(4):639–44; Rice K D, Tanaka R D, Katz B A, Numerof R P, Moore W R, Inhibitors of tryptase for the treatment of mast cell-mediated diseases, Curr Pharm Des 1998 October;4(5):381–96; Materson B J, Will angiotensin converting enzyme genotype, receptor mutation identification, and other miracles of molecular biology permit reduction of NNT Am J Hypertens 1998 August;11(8 Pt 2):138S–142S Metalloprotease The metalloproteases may be one of the older classes of proteinases and are found in bacteria, fungi as well as in higher organisms. They differ widely in their sequences and their structures but the great majority of enzymes contain a zinc atom which is catalytically active. In some cases, zinc may be replaced by another metal such as cobalt or nickel without loss of the activity. Bacterial thermolysin has been well characterized and its crystallographic structure indicates that zinc is bound by two histidines and one glutamic acid. Many enzymes contain the sequence HEXXH, which provides two histidine ligands for the zinc whereas the third ligand is either a glutamic acid (thermolysin, neprilysin, alanyl aminopeptidase) or a histidine (astacin). Other families exhibit a distinct mode of binding of the Zn atom. The catalytic mechanism leads to the formation of a non covalent tetrahedral intermediate after the attack of a zinc-bound water molecule on the carbonyl group of the scissile bond. This intermediate is further decomposed by transfer of the glutamic acid proton to the leaving group.

Metalloproteases contain a catalytic zinc metal center which participates in the hydrolysis of the peptide backbone (reviewed in Power and Harper, in Protease Inhibitors, A. J. Barrett and G. Salversen (eds.) Elsevier, Amsterdam, 1986, p. 219). The active zinc center differentiates some of these proteases from calpains and trypsins whose activities are dependent upon the presence of calcium. Examples of metalloproteases include carboxypeptidase A, carboxypeptidase B, and thermolysin.

Metalloproteases have been isolated from a number of procaryotic and eucaryotic sources, e.g. *Bacillus subtilis* (McConn et al., 1964, J. Biol. Chem. 239:3706); *Bacillus megaterium; Serratia* (Miyata et al., 1971, Agr. Biol. Chem. 35:460); *Clostridium bifermentans* (MacFarlane et al., 1992, App. Environ. Microbiol. 58:1195–1200), *Legionella pneumophila* (Moffat et al., 1994, Infection and Immunity 62:751–3). In particular, acidic metalloproteases have been isolated from broad-banded copperhead venoms (Johnson and Ownby, 1993, Int. J. Biochem. 25:267–278), rattlesnake venoms (Chlou et al., 1992, Biochem. Biophys. Res. Commun. 187:389–396) and articular cartilage (Treadwell et al., 1986, Arch. Biochem. Biophys. 251:715–723). Neutral metalloproteases, specifically those having optimal activity at neutral pH have, for example, been isolated from *Aspergillus sojae* (Sekine, 1973, Agric. Biol. Chem. 37:1945–1952). Neutral metalloproteases obtained from *Aspergillus* have been classified into two groups, npI and npII (Sekine, 1972, Agric. Biol. Chem. 36:207–216). So far, success in obtaining amino acid sequence information from these fungal neutral metalloproteases has been limited. An npII metalloprotease isolated from *Aspergillus oryzae* has been cloned based on amino acid sequence presented in the literature (Tatsumi et al., 1991, Mol. Gen. Genet. 228:97–103). However, to date, no npI fungal metalloprotease has been cloned or sequenced. Alkaline metalloproteases, for example, have been isolated from *Pseudomonas aeruginosa* (Baumann et al., 1993, EMBO J 12:3357–3364) and the insect pathogen *Xenorhabdus luminescens* (Schmidt et al., 1998, Appl. Environ. Microbiol. 54:2793–2797).

Metalloproteases have been devided into several distinct families based primarily on activity and sturcture: 1) water nucleophile; water bound by single zinc ion ligated to two His (within the motif HEXXH) and Glu, His or Asp; 2) water nucleophile; water bound by single zinc ion ligated to His, Glu (within the motif HXXE) and His; 3) water nucleophile; water bound by single zinc ion ligated to His, Asp and His; 4) Water nucleophile; water bound by single zinc ion ligated to two His (within the motif HXXEH) and Glu and 5) water nucleophile; water bound by two zinc ions ligated by Lys, Asp, Asp, Asp, Glu.

Examples of members of the metalloproteinase family include, but are not limited to, membrane alanyl aminopeptidase (*Homo sapiens*), germinal peptidyl-dipeptidase A (*Homo sapiens*), thimet oligopeptidase (*Rattus norvegicus*), oligopeptidase F (*Lactococcus lactis*), mycolysin (*Streptomyces cacaoi*), immune inhibitor A (*Bacillus thuringiensis*), snapalysin (*Streptomyces lividans*), leishmanolysin (*Leishmania major*), microbial collagenase (*Vibrio alginolyticus*), microbial collagenase, class I (*Clostridium perfringens*), collagenase 1 (*Homo sapiens*), serralysin (*Serratia marcescens*), fragilysin (*Bacteroides fragilis*), gametolysin (*Chlamydomonas reinhardtii*), astacin (*Astacus fluviatilis*), adamalysin (*Crotalus adamanteus*), ADAM 10 (*Bos taurus*), neprilysin (*Homo sapiens*), carboxypeptidase A (*Homo sapiens*), carboxypeptidase E (*Bos taurus*), gamma-D-glutamyl-(L)-meso-diaminopimelate peptidase I (*Bacillus sphaericus*), vanY D-Ala-D-Ala carboxypeptidase (*Enterococcus faecium*), endolysin (bacteriophage A118), pitrilysin (*Escherichia coli*), mitochondrial processing peptidase (*Saccharomyces cerevisiae*), leucyl aminopeptidase (*Bos taurus*), aminopeptidase I (*Saccharomyces cerevisiae*), membrane dipeptidase (*Homo sapiens*), glutamate carboxypeptidase (*Pseudomonas* sp.), Gly-X carboxypeptidase (*Saccharomyces cerevisiae*), O-sialoglycoprotein endopeptidase (*Pasteurella haemolytica*), beta-lytic metalloendopeptidase (*Achromobacter lyticus*), methionyl aminopeptidase I (*Escherichia coli*), X-Pro aminopeptidase (*Escherichia coli*), X-His dipeptidase (*Escherichia coli*), IgA1-specific metalloendopeptidase (*Streptococcus sanguis*), tentoxilysin (*Clostridium tetani*), leucyl aminopeptidase (*Vibrio proteolyticus*), aminopeptidase (*Streptomyces griseus*), IAP aminopeptidase (*Escherichia coli*), aminopeptidase T (*Thermus aquaticus*), hyicolysin (*Staphylococcus hyicus*), carboxypeptidase Taq (*Thermus aquaticus*), anthrax lethal factor (*Bacillus anthracis*), penicillolysin (*Penicillium citrinum*), fungalysin (*Aspergillus fumigatus*), lysostaphin (*Staphylococcus simulans*), beta-aspartyl dipeptidase (*Escherichia coli*), carboxypeptidase Ss1 (*Sulfolobus solfataricus*), FtsH endopeptidase (*Escherichia coli*), glutamyl aminopeptidase (*Lactococcus lactis*), cytophagalysin (*Cytophaga* sp.), metalloendopeptidase (vaccinia virus), VanX D-Ala-D-Ala dipeptidase (*Enterococcus faecium*), Ste24p endopeptidase (*Saccharomyces cerevisiae*), dipeptidyl-peptidase III (*Rattus norvegicus*), S2P protease (*Homo sapiens*), sporulation factor SpoIVFB (*Bacillus subtilis*), and HYBD endopeptidase (*Escherichia coli*).

Metalloproteases have been found to have a number of uses. For example, there is strong evidence that a metalloprotease is involved in the in vivo proteolytic processing of the vasoconstrictor, endothelin-1. Rat metalloprotease has been found to be involved in peptide hormone processing. One important subfamily of the metalloproteases are the matrix metalloproteases.

A number of diseases are thought to be mediated by excess or undesired metalloprotease activity or by an imbalance in the ratio of the various members of the protease family of proteins. These include: a) osteoarthritis (Woessner, et al., J. Biol. Chem. 259(6), 3633, 1984; Phadke, et al., J. Rheumatol. 10, 852, 1983), b) rheumatoid arthritis (Mullins, et al., Biochim. Biophys. Acta 695, 117, 1983; Woolley, et al., Arthritis Rheum. 20, 1231, 1977; Gravallese, et al., Arthritis Rheum. 34, 1076, 1991), c) septic arthritis (Williams, et al., Arthritis Rheum. 33, 533, 1990), d) tumor metastasis (Reich, et al., Cancer Res. 48, 3307, 1988, and Matrisian, et al., Proc. Nat'l. Acad. Sci., USA 83, 9413, 1986), e) periodontal diseases (Overall, et al., J. Periodontal Res. 22, 81, 1987), f) corneal ulceration (Bums, et al., Invest. Opthalmol. Vis. Sci. 30, 1569, 1989), g) proteinuria (Baricos, et al., Biochem. J. 254, 609, 1988), h) coronary thrombosis from atherosclerotic plaque rupture (Henney, et al., Proc. Nat'l. Acad. Sci., USA 88, 8154–8158, 1991), i) aneurysmal aortic disease (Vine, et al., Clin. Sci. 81, 233, 1991), j) birth control (Woessner, et al., Steroids 54, 491, 1989), k) dystrophobic epidermolysis bullosa (Kronberger, et al., J. Invest. Dermatol. 79, 208, 1982), and l) degenerative cartilage loss following traumatic joint injury, m) conditions leading to inflammatory responses, osteopenias mediated by MMP activity, n) tempero mandibular joint disease, o) demyelating diseases of the nervous system (Chantry, et al., J. Neurochem. 50, 688, 1988).

Zinc Proteases

Zinc proteases are a diverse group of enzymes that cleave proteins at specific sites. These enzymes belong to the group of metalloproteases, they contain zinc at their active sites. The protease of the present invention is homologous to hatching proteases of invertebrates and collagenases of mammals.

The protease of the present invention may be involved in cleavage of structural proteins in extracellular reticulum. Its activity may affect cell division and differentiation. Choriolytic hatching enzymes are expressed during development, their production virtually stops after hatching. There are sometimes isolated from chorioallantoic membrane. Zinc proteases often are synthesized as inactive precursors that are activated by autoproteolysis; twenty to thirty amino acids are removed from their N-termini as a result of activation.

Another group of metalloproteases closely related to astacin are meprins. These are expressed in epithelia of kidneys and intestine as well as in developing neural tissue. The meprins are overexpressed in some tumors, which enables their progression into stroma.

The protease of the present invention contains a motif present in active site of some metalloproteinases, HExxH. Sequence HELMHVLGFWHEH may represent its active site. Using this information, one can develop competitive inhibitors, which may be used to treat cancers.

For a review of zinc proteases and choriolytic hatching enzymes, see: Yasumasu S, et al., *Dev Biol* 1992 October; 153(2):250–8; Yasumasu S, et al., *Eur J Biochem* 1996 May 1;237(3):752–8; Kohler D, et al., *FEBS Lett* 2000 January 7;465(1):2–7; and Lottaz D, et al., *Cancer Res* 1999 March 1;59(5):1127–33.

Aspartic Protease

Aspartic proteases have been divided into several distinct families based primarily on activity and structure. These include 1) water nucleophile; water bound by two Asp from monomer or dimer; all endopeptidases, from eukaryote organisms, viruses or virus-like organisms and 2) endopeptidases that are water nucleophile and are water bound by Asp and Asn.

Most of aspartic proteases belong to the pepsin family. The pepsin family includes digestive enzymes such as pepsin and chymosin as well as lysosomal cathepsins D and processing enzymes such as renin, and certain fungal proteases (penicillopepsin, rhizopuspepsin, endothiapepsin). A second family comprises viral proteases such as the protease from the AIDS virus (HIV) also called retropepsin. Crystallographic studies have shown that these enzymes are bilobed molecules with the active site located between two homologous lobes. Each lobe contributes one aspartate residue of the catalytically active diad of aspartates. These two aspartyl residues are in close geometric proximity in the active molecule and one aspartate is ionized whereas the second one is unionized at the optimum pH range of 2–3. Retropepsins, are monomeric, i.e carry only one catalytic aspartate and then dimerization is required to form an active enzyme.

In contrast to serine and cysteine proteases, catalysis by aspartic protease do not involve a covalent intermediate though a tetrahedral intermediate exists. The nucleophilic attack is achieved by two simultaneous proton transfer: one from a water molecule to the diad of the two carboxyl groups and a second one from the diad to the carbonyl oxygen of the substrate with the concurrent CO—NH bond cleavage. This general acid-base catalysis, which may be called a "push-pull" mechanism leads to the formation of a non covalent neutral tetrahedral intermediate.

Examples of the aspartic protease family of proteins include, but are not limited to, pepsin A (*Homo sapiens*), HIV1 retropepsin (human immunodeficiency virus type 1), endopeptidase (cauliflower mosaic virus), baciliform virus putative protease (rice tungro baciliform virus), aspergillopepsin II (*Aspergillus niger*), thermopsin (*Sulfolobus acidocaldarius*), nodavirus endopeptidase (flock house virus), pseudomonapepsin (*Pseudomonas* sp. 101), signal peptidase II (*Escherichia coli*), polyprotein peptidase (human spumaretrovirus), copia transposon (*Drosophila melanogaster*), SIRE-1 peptidase (*Glycine max*), retrotransposon bs1 endopeptidase (*Zea mays*), retrotransposon peptidase (*Drosophila buzzatii*), Tas retrotransposon peptidase (*Ascaris lumbricoides*), Pao retrotransposon peptidase (*Bombyx mori*), putative proteinase of Skippy retrotransposon (*Fusarium oxysporum*), tetravirus endopeptidase (Nudaurelia capensis omega virus), presenilin 1 (*Homo sapiens*).

Proteases and Cancer

Proteases are critical elements at several stages in the progression of metastatic cancer. In this process, the proteolytic degradation of structural protein in the basal membrane allows for expansion of a tumor in the primary site, evasion from this site as well as homing and invasion in distant, secondary sites. Also, tumor induced angiogenesis is required for tumor growth and is dependent on proteolytic tissue remodeling. Transfection experiments with various types of proteases have shown that the matrix metalloproteases play a dominant role in these processes in particular gelatinases A and B (MMP-2 and MMP-9, respectively). For an overview of this field see Mullins, et al., Biochim. Biophys. Acta 695, 177, 1983; Ray, et al., Eur. Respir. J. 7, 2062, 1994; Birkedal-Hansen, et al., Crit. Rev. Oral Biol. Med. 4, 197, 1993.

Furthermore, it was demonstrated that inhibition of degradation of extracellular matrix by the native matrix metalloprotease inhibitor TIMP-2 (a protein) arrests cancer growth (DeClerck, et al., Cancer Res. 52, 701, 1992) and that TIMP-2 inhibits tumor-induced angiogenesis in experimental systems (Moses, et al. Science 248, 1408, 1990). For a review, see DeClerck, et al., Ann. N.Y. Acad. Sci. 732, 222, 1994. It was further demonstrated that the synthetic matrix metalloprotease inhibitor batimastat when given intraperitoneally inhibits human colon tumor growth and spread in an orthotopic model in nude mice (Wang, et al. Cancer Res. 54, 4726, 1994) and prolongs the survival of mice bearing human ovarian carcinoma xenografts (Davies, et. al., Cancer Res. 53, 2087, 1993). The use of this and related compounds has been described in Brown, et al., WO-9321942 A2.

There are several patents and patent applications claiming the use of metalloproteinase inhibitors for the retardation of metastatic cancer, promoting tumor regression, inhibiting cancer cell proliferation, slowing or preventing cartilage loss associated with osteoarthritis or for treatment of other diseases as noted above (e.g. Levy, et al., WO-9519965 A1; Beckett, et al., WO-9519956 A1; Beckett, et al., WO-9519957 A1; Beckett, et al., WO-9519961 A1; Brown, et al., WO-9321942 A2; Crimmin, et al., WO-9421625 A1; Dickens, et al., U.S. Pat. No. 4,599,361; Hughes, et al., U.S. Pat. No. 5,190,937; Broadhurst, et al., EP 574758 A1; Broadhurst, et al., EP 276436; and Myers, et al., EP 520573 A1.

Protease proteins, particularly members of the choriolytic hatching protease subfamily, are a major target for drug action and development. Accordingly, it is valuable to the field of pharmaceutical development to identify and characterize previously unknown members of this subfamily of protease proteins. The present invention advances the state of the art by providing a previously unidentified human protease proteins that have homology to members of the choriolytic hatching protease subfamily.

SUMMARY OF THE INVENTION

The present invention is based in part on the identification of amino acid sequences of human protease peptides and proteins that are related to the choriolytic hatching protease subfamily, as well as allelic variants and other mammnalian orthologs thereof. These unique peptide sequences, and nucleic acid sequences that encode these peptides, can be used as models for the development of human therapeutic targets, aid in the identification of therapeutic proteins, and serve as targets for the development of human therapeutic agents that modulate protease activity in cells and tissues that express the protease. Experimental data as provided in FIG. 1 indicates expression in the human fetus, pooled human melanocyte tissue, fetal heart, and pregnant uterus.

DESCRIPTION OF THE FIGURE SHEETS

FIG. 1 provides the nucleotide sequence of a cDNA molecule or transcript sequence that encodes the protease protein of the present invention. (SEQ ID NO:1) In addition, structure and functional information is provided, such as ATG start, stop and tissue distribution, where available, that allows one to readily determine specific uses of inventions based on this molecular sequence. Experimental data as provided in FIG. 1 indicates expression in the human fetus, pooled human melanocyte tissue, fetal heart, and pregnant uterus.

FIG. 2 provides the predicted amino acid sequence of the protease of the present invention. (SEQ ID NO:2) In addition structure and functional information such as protein family, function, and modification sites is provided where available, allowing one to readily determine specific uses of inventions based on this molecular sequence.

FIG. 3 provides genomic sequences that span the gene encoding the protease protein of the present invention. (SEQ ID NO:3) In addition structure and functional information, such as intron/exon structure, promoter location, etc., is provided where available, allowing one to readily determine specific uses of inventions based on this molecular sequence.

DETAILED DESCRIPTION OF THE INVENTION

General Description

The present invention is based on the sequencing of the human genome. During the sequencing and assembly of the human genome, analysis of the sequence information revealed previously unidentified fragments of the human genome that encode peptides that share structural and/or sequence homology to protein/peptide/domains identified and characterized within the art as being a protease protein or part of a protease protein and are related to the choriolytic hatching protease subfamily. Utilizing these sequences, additional genomic sequences were assembled and transcript and/or cDNA sequences were isolated and characterized. Based on this analysis, the present invention provides amino acid sequences of human protease peptides and proteins that are related to the choriolytic hatching protease subfamily, nucleic acid sequences in the form of transcript sequences, cDNA sequences and/or genomic sequences that encode these protease peptides and proteins, nucleic acid variation (allelic information), tissue distribution of expression, and information about the closest art known protein/peptide/domain that has structural or sequence homology to the protease of the present invention.

In addition to being previously unknown, the peptides that are provided in the present invention are selected based on their ability to be used for the development of commercially important products and services. Specifically, the present peptides are selected based on homology and/or structural relatedness to known protease proteins of the choriolytic hatching protease subfamily and the expression pattern observed. Experimental data as provided in FIG. 1 indicates expression in the human fetus, pooled human melanocyte tissue, fetal heart, and pregnant uterus. The art has clearly established the commercial importance of members of this family of proteins and proteins that have expression patterns similar to that of the present gene. Some of the more specific features of the peptides of the present invention, and the uses thereof, are described herein, particularly in the Background of the Invention and in the annotation provided in the Figures, and/or are known within the art for each of the known choriolytic hatching protease family or subfamily of protease proteins.

Specific Embodiments

Peptide Molecules

The present invention provides nucleic acid sequences that encode protein molecules that have been identified as being members of the protease family of proteins and are related to the choriolytic hatching protease subfamily (protein sequences are provided in FIG. 2, transcript/cDNA sequences are provided in FIG. 1 and genomic sequences are provided in FIG. 3). The peptide sequences provided in FIG. 2, as well as the obvious variants described herein, particularly allelic variants as identified herein and using the information in FIG. 3, will be referred herein as the protease peptides of the present invention, protease peptides, or peptides/proteins of the present invention.

The present invention provides isolated peptide and protein molecules that consist of, consist essentially of, or comprise the amino acid sequences of the protease peptides disclosed in the FIG. 2, (encoded by the nucleic acid molecule shown in FIG. 1, transcript/cDNA or FIG. 3, genomic sequence), as well as all obvious variants of these peptides that are within the art to make and use. Some of these variants are described in detail below.

As used herein, a peptide is said to be "isolated" or "purified" when it is substantially free of cellular material or free of chemical precursors or other chemicals. The peptides of the present invention can be purified to homogeneity or other degrees of purity. The level of purification will be based on the intended use. The critical feature is that the preparation allows for the desired function of the peptide, even if in the presence of considerable amounts of other components (the features of an isolated nucleic acid molecule is discussed below).

In some uses, "substantially free of cellular material" includes preparations of the peptide having less than about 30% (by dry weight) other proteins (i.e., contaminating protein), less than about 20% other proteins, less than about 10% other proteins, or less than about 5% other proteins. When the peptide is recombinantly produced, it can also be substantially free of culture medium, i.e., culture medium represents less than about 20% of the volume of the protein preparation.

The language "substantially free of chemical precursors or other chemicals" includes preparations of the peptide in which it is separated from chemical precursors or other chemicals that are involved in its synthesis. In one embodiment, the language "substantially free of chemical precursors or other chemicals" includes preparations of the protease peptide having less than about 30% (by dry weight) chemical precursors or other chemicals, less than about 20% chemical precursors or other chemicals, less than about 10% chemical precursors or other chemicals, or less than about 5% chemical precursors or other chemicals.

The isolated protease peptide can be purified from cells that naturally express it, purified from cells that have been altered to express it (recombinant), or synthesized using known protein synthesis methods. Experimental data as provided in FIG. 1 indicates expression in the human fetus, pooled human melanocyte tissue, fetal heart, and pregnant uterus. For example, a nucleic acid molecule encoding the protease peptide is cloned into an expression vector, the expression vector introduced into a host cell and the protein expressed in the host cell. The protein can then be isolated from the cells by an appropriate purification scheme using standard protein purification techniques. Many of these techniques are described in detail below.

Accordingly, the present invention provides proteins that consist of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). The amino acid sequence of such a protein is provided in FIG. 2. A protein consists of an amino acid sequence when the amino acid sequence is the final amino acid sequence of the protein.

The present invention further provides proteins that consist essentially of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein consists essentially of an amino acid sequence when such an amino acid sequence is present with only a few additional amino acid residues, for example from about 1 to about 100 or so additional residues, typically from 1 to about 20 additional residues in the final protein.

The present invention further provides proteins that comprise the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein comprises an amino acid sequence when the amino acid sequence is at least part of the final amino acid sequence of the protein. In such a fashion, the protein can be only the peptide or have additional amino acid molecules, such as amino acid residues (contiguous encoded sequence) that are naturally associated with it or heterologous amino acid residues/peptide sequences. Such a protein can have a few additional amino acid residues or can comprise several hundred or more additional amino acids. The preferred classes of proteins that are comprised of the protease peptides of the present invention are the naturally occurring mature proteins. A brief description of how various types of these proteins can be made/isolated is provided below.

The protease peptides of the present invention can be attached to heterologous sequences to form chimeric or fusion proteins. Such chimeric and fusion proteins comprise a protease peptide operatively linked to a heterologous protein having an amino acid sequence not substantially homologous to the protease peptide. "Operatively linked" indicates that the protease peptide and the heterologous protein are fused in-frame. The heterologous protein can be fused to the N-terminus or C-terminus of the protease peptide.

In some uses, the fusion protein does not affect the activity of the protease peptide per se. For example, the fusion protein can include, but is not limited to, enzymatic fusion proteins, for example beta-galactosidase fusions, yeast two-hybrid GAL fusions, poly-His fusions, MYC-tagged, HI-tagged and Ig fusions. Such fusion proteins, particularly poly-His fusions, can facilitate the purification of recombinant protease peptide. In certain host cells (e.g., mammalian host cells), expression and/or secretion of a protein can be increased by using a heterologous signal sequence.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al., *Current Protocols in Molecular Biology*, 1992). Moreover, many expression vectors are commercially available that already encode a fusion moiety (e.g., a GST protein). A protease peptide-encoding nucleic acid can be cloned into such an expression vector such that the fusion moiety is linked in-frame to the protease peptide.

As mentioned above, the present invention also provides and enables obvious variants of the amino acid sequence of the proteins of the present invention, such as naturally occurring mature forms of the peptide, allelic/sequence variants of the peptides, non-naturally occurring recombinantly derived variants of the peptides, and orthologs and paralogs of the peptides. Such variants can readily be generated using art-known techniques in the fields of recombinant nucleic acid technology and protein biochemistry. It is understood, however, that variants exclude any amino acid sequences disclosed prior to the invention.

Such variants can readily be identified/made using molecular techniques and the sequence information disclosed herein. Further, such variants can readily be distinguished from other peptides based on sequence and/or structural homology to the protease peptides of the present invention. The degree of homology/identity present will be based primarily on whether the peptide is a functional variant or non-functional variant, the amount of divergence present in the paralog family and the evolutionary distance between the orthologs.

To determine the percent identity of two amino acid sequences or two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, at least 30%, 40%, 50%, 60%, 70%, 80%, or 90% or more of the length of a reference sequence is aligned for comparison purposes. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity and similarity between two sequences can be accomplished using a mathematical algorithm. (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data, Part 1*, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991). In a preferred embodiment, the percent identity between two amino acid sequences is determined using the Needleman and Wunsch (*J. Mol. Biol.* (48):444–453 (1970)) algorithm which has been incorporated into the GAP program in the GCG software package (available at http://www.gcg.com), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (Devereux, J., et al., *Nucleic Acids Res.* 12(1):387 (1984)) (available at http://www.gcg.com), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Myers and W. Miller (CABIOS, 4:11–17 (1989)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against sequence databases to, for example, identify other family members or related sequences. Such searches can be performed using the NBLAST and XBLAST programs (version 2.0) of Altschul, et al. (*J. Mol. Biol.* 215:403–10 (1990)). BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the proteins of the invention. To obtain gapped alignments for comparison purposes, Gapped BLAST can be utilized as described in Altschul et al. (*Nucleic Acids Res.* 25(17):3389–3402 (1997)). When utilizing BLAST and gapped BLAST programs, the default parameters of the respective programs (e.g., XBLAST and NBLAST) can be used.

Full-length pre-processed forms, as well as mature processed forms, of proteins that comprise one of the peptides of the present invention can readily be identified as having complete sequence identity to one of the protease peptides of the present invention as well as being encoded by the same genetic locus as the protease peptide provided herein.

Allelic variants of a protease peptide can readily be identified as being a human protein having a high degree (significant) of sequence homology/identity to at least a portion of the protease peptide as well as being encoded by the same genetic locus as the protease peptide provided herein. Genetic locus can readily be determined based on the genomic information provided in FIG. 3, such as the genomic sequence mapped to the reference human. As used herein, two proteins (or a region of the proteins) have significant homology when the amino acid sequences are typically at least about 70–80%, 80–90%, and more typically at least about 90–95% or more homologous. A significantly homologous amino acid sequence, according to the present invention, will be encoded by a nucleic acid sequence that will hybridize to a protease peptide encoding nucleic acid molecule under stringent conditions as more fully described below.

Paralogs of a protease peptide can readily be identified as having some degree of significant sequence homology/identity to at least a portion of the protease peptide, as being encoded by a gene from humans, and as having similar activity or function. Two proteins will typically be considered paralogs when the amino acid sequences are typically at least about 60% or greater, and more typically at least about 70% or greater homology through a given region or domain. Such paralogs will be encoded by a nucleic acid sequence that will hybridize to a protease peptide encoding nucleic acid molecule under moderate to stringent conditions as more fully described below.

Orthologs of a protease peptide can readily be identified as having some degree of significant sequence homology/identity to at least a portion of the protease peptide as well as being encoded by a gene from another organism. Preferred orthologs will be isolated from mammals, preferably primates, for the development of human therapeutic targets and agents. Such orthologs will be encoded by a nucleic acid sequence that will hybridize to a protease peptide encoding nucleic acid molecule under moderate to stringent conditions, as more fully described below, depending on the degree of relatedness of the two organisms yielding the proteins.

Non-naturally occurring variants of the protease peptides of the present invention can readily be generated using recombinant techniques. Such variants include, but are not limited to deletions, additions and substitutions in the amino acid sequence of the protease peptide. For example, one class of substitutions are conserved amino acid substitution. Such substitutions are those that substitute a given amino acid in a protease peptide by another amino acid of like characteristics. Typically seen as conservative substitutions are the replacements, one for another, among the aliphatic amino acids Ala, Val, Leu, and Ile; interchange of the hydroxyl residues Ser and Thr; exchange of the acidic residues Asp and Glu; substitution between the amide residues Asn and Gln; exchange of the basic residues Lys and Arg; and replacements among the aromatic residues Phe and Tyr. Guidance concerning which amino acid changes are likely to be phenotypically silent are found in Bowie et al., *Science* 247:1306–1310 (1990).

Variant protease peptides can be fully functional or can lack function in one or more activities, e.g. ability to bind substrate, ability to cleave substrate, ability to participate in a signaling pathway, etc. Fully functional variants typically contain only conservative variation or variation in non-critical residues or in non-critical regions. FIG. 2 provides the result of protein analysis and can be used to identify critical domains/regions. Functional variants can also contain substitution of similar amino acids that result in no change or an insignificant change in function. Alternatively, such substitutions may positively or negatively affect function to some degree.

Non-functional variants typically contain one or more non-conservative amino acid substitutions, deletions, insertions, inversions, or truncation or a substitution, insertion, inversion, or deletion in a critical residue or critical region.

Amino acids that are essential for function can be identified by methods known in the art, such as site-directed mutagenesis or alanine-scanning mutagenesis (Cunningham et al., *Science* 244:1081–1085 (1989)), particularly using the results provided in FIG. 2. The latter procedure introduces single alanine mutations at every residue in the molecule. The resulting mutant molecules are then tested for biological activity such as protease activity or in assays such as an in vitro proliferative activity. Sites that are critical for binding partner/substrate binding can also be determined by structural analysis such as crystallization, nuclear magnetic resonance or photoaffinity labeling (Smith et al., *J. Mol. Biol.* 224:899–904 (1992); de Vos et al. *Science* 255:306–312 (1992)).

The present invention further provides fragments of the protease peptides, in addition to proteins and peptides that comprise and consist of such fragments, particularly those comprising the residues identified in FIG. 2. The fragments to which the invention pertains, however, are not to be construed as encompassing fragments that may be disclosed publicly prior to the present invention.

As used herein, a fragment comprises at least 8, 10, 12, 14, 16, or more contiguous amino acid residues from a protease peptide. Such fragments can be chosen based on the ability to retain one or more of the biological activities of the protease peptide or could be chosen for the ability to perform a function, e.g. bind a substrate or act as an immunogen. Particularly important fragments are biologically active fragments, peptides that are, for example, about 8 or more amino acids in length. Such fragments will typically comprise a domain or motif of the protease peptide, e.g., active site, a transmembrane domain or a substrate-binding domain. Further, possible fragments include, but are not limited to, domain or motif containing fragments, soluble peptide fragments, and fragments containing immunogenic structures. Predicted domains and functional sites are readily identifiable by computer programs well known and readily available to those of skill in the art (e.g., PROSITE analysis). The results of one such analysis are provided in FIG. 2.

Polypeptides often contain amino acids other than the 20 amino acids commonly referred to as the 20 naturally occurring amino acids. Further, many amino acids, including the terminal amino acids, may be modified by natural processes, such as processing and other post-translational modifications, or by chemical modification techniques well known in the art. Common modifications that occur naturally in protease peptides are described in basic texts, detailed monographs, and the research literature, and they are well known to those of skill in the art (some of these features are identified in FIG. 2).

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as *Proteins—Structure and Molecular Properties*, 2nd Ed., T. E. Creighton, W. H. Freeman and Company, New York (1993). Many detailed reviews are available on this subject, such as by Wold, F., *Posttranslational Covalent Modification of Proteins*, B. C. Johnson, Ed., Academic Press, New York 1–12 (1983); Seifter et al. (*Meth. Enzymol.* 182: 626–646 (1990)) and Rattan et al. (*Ann. N.Y. Acad. Sci.* 663:48–62 (1992)).

Accordingly, the protease peptides of the present invention also encompass derivatives or analogs in which a substituted amino acid residue is not one encoded by the genetic code, in which a substituent group is included, in which the mature protease peptide is fused with another compound, such as a compound to increase the half-life of the protease peptide (for example, polyethylene glycol), or in which the additional amino acids are fused to the mature protease peptide, such as a leader or secretory sequence or a sequence for purification of the mature protease peptide or a pro-protein sequence.

Protein/Peptide Uses

The proteins of the present invention can be used in substantial and specific assays related to the functional information provided in the Figures; to raise antibodies or to elicit another immune response; as a reagent (including the labeled reagent) in assays designed to quantitatively determine levels of the protein (or its binding partner or ligand) in biological fluids; and as markers for tissues in which the corresponding protein is preferentially expressed (either constitutively or at a particular stage of tissue differentiation or development or in a disease state). Where the protein binds or potentially binds to another protein or ligand (such as, for example, in a protease-effector protein interaction or protease-ligand interaction), the protein can be used to identify the binding partner/ligand so as to develop a system to identify inhibitors of the binding interaction. Any or all of these uses are capable of being developed into reagent grade or kit format for commercialization as commercial products.

Methods for performing the uses listed above are well known to those skilled in the art. References disclosing such methods include "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

The potential uses of the peptides of the present invention are based primarily on the source of the protein as well as the class/action of the protein. For example, proteases isolated from humans and their human/mammalian orthologs serve as targets for identifying agents for use in mammalian therapeutic applications, e.g. a human drug, particularly in modulating a biological or pathological response in a cell or tissue that expresses the protease. Experimental data as provided in FIG. 1 indicates that protease proteins of the present invention are expressed in the human fetus, pooled human melanocyte tissue, fetal heart, and pregnant uterus. Specifically, a virtual northern blot shows expression in the human fetus, pooled human melanocyte tissue, fetal heart, and pregnant uterus. A large percentage of pharmaceutical agents are being developed that modulate the activity of protease proteins, particularly members of the choriolytic hatching protease subfamily (see Background of the Invention). The structural and functional information provided in the Background and Figures provide specific and substantial uses for the molecules of the present invention, particularly in combination with the expression information provided in FIG. 1. Experimental data as provided in FIG. 1 indicates expression in the human fetus, pooled human melanocyte tissue, fetal heart, and pregnant uterus. Such uses can readily be determined using the information provided herein, that which is known in the art, and routine experimentation.

The proteins of the present invention (including variants and fragments that may have been disclosed prior to the present invention) are useful for biological assays related to proteases that are related to members of the choriolytic hatching protease subfamily. Such assays involve any of the known protease functions or activities or properties useful for diagnosis and treatment of protease-related conditions that are specific for the subfamily of proteases that the one of the present invention belongs to, particularly in cells and tissues that express the protease. Experimental data as provided in FIG. 1 indicates that protease proteins of the present invention are expressed in the human fetus, pooled human melanocyte tissue, fetal heart, and pregnant uterus.

Specifically, a virtual northern blot shows expression in the human fetus, pooled human melanocyte tissue, fetal heart, and pregnant uterus.

The proteins of the present invention are also useful in drug screening assays, in cell-based or cell-free systems. Cell-based systems can be native, i.e., cells that normally express the protease, as a biopsy or expanded in cell culture. Experimental data as provided in FIG. 1 indicates expression in the human fetus, pooled human melanocyte tissue, fetal heart, and pregnant uterus. In an alternate embodiment, cell-based assays involve recombinant host cells expressing the protease protein.

The polypeptides can be used to identify compounds that modulate protease activity of the protein in its natural state or an altered form that causes a specific disease or pathology associated with the protease. Both the proteases of the present invention and appropriate variants and fragments can be used in high-throughput screens to assay candidate compounds for the ability to bind to the protease. These compounds can be further screened against a functional protease to determine the effect of the compound on the protease activity. Further, these compounds can be tested in animal or invertebrate systems to determine activity/effectiveness. Compounds can be identified that activate (agonist) or inactivate (antagonist) the protease to a desired degree.

Further, the proteins of the present invention can be used to screen a compound for the ability to stimulate or inhibit interaction between the protease protein and a molecule that normally interacts with the protease protein, e.g. a substrate or a component of the signal pathway that the protease protein normally interacts (for example, a protease). Such assays typically include the steps of combining the protease protein with a candidate compound under conditions that allow the protease protein, or fragment, to interact with the target molecule, and to detect the formation of a complex between the protein and the target or to detect the biochemical consequence of the interaction with the protease protein and the target, such as any of the associated effects of signal transduction such as protein cleavage, cAMP turnover, and adenylate cyclase activation, etc.

Candidate compounds include, for example, 1) peptides such as soluble peptides, including Ig-tailed fusion peptides and members of random peptide libraries (see, e.g., Lam et al., *Nature* 354:82–84 (1991); Houghten et al., *Nature* 354:84–86 (1991)) and combinatorial chemistry-derived molecular libraries made of D- and/or L-configuration amino acids; 2) phosphopeptides (e.g., members of random and partially degenerate, directed phosphopeptide libraries, see, e.g., Songyang et al., *Cell* 72:767–778 (1993)); 3) antibodies (e.g., polyclonal, monoclonal, humanized, anti-idiotypic, chimeric, and single chain antibodies as well as Fab, $F(ab')_2$, Fab expression library fragments, and epitope-binding fragments of antibodies); and 4) small organic and inorganic molecules (e.g., molecules obtained from combinatorial and natural product libraries).

One candidate compound is a soluble fragment of the receptor that competes for substrate binding. Other candidate compounds include mutant proteases or appropriate fragments containing mutations that affect protease function and thus compete for substrate. Accordingly, a fragment that competes for substrate, for example with a higher affinity, or a fragment that binds substrate but does not allow release, is encompassed by the invention.

The invention further includes other end point assays to identify compounds that modulate (stimulate or inhibit) protease activity. The assays typically involve an assay of events in the signal transduction pathway that indicate protease activity. Thus, the cleavage of a substrate, inactivation/activation of a protein, a change in the expression of genes that are up- or down-regulated in response to the protease protein dependent signal cascade can be assayed.

Any of the biological or biochemical functions mediated by the protease can be used as an endpoint assay. These include all of the biochemical or biochemical/biological events described herein, in the references cited herein, incorporated by reference for these endpoint assay targets, and other functions known to those of ordinary skill in the art or that can be readily identified using the information provided in the Figures, particularly FIG. 2. Specifically, a biological function of a cell or tissues that expresses the protease can be assayed. Experimental data as provided in FIG. 1 indicates that protease proteins of the present invention are expressed in the human fetus, pooled human melanocyte tissue, fetal heart, and pregnant uterus. Specifically, a virtual northern blot shows expression in the human fetus, pooled human melanocyte tissue, fetal heart, and pregnant uterus.

Binding and/or activating compounds can also be screened by using chimeric protease proteins in which the amino terminal extracellular domain, or parts thereof, the entire transmembrane domain or subregions, such as any of the seven transmembrane segments or any of the intracellular or extracellular loops and the carboxy terminal intracellular domain, or parts thereof, can be replaced by heterologous domains or subregions. For example, a substrate-binding region can be used that interacts with a different substrate then that which is recognized by the native protease. Accordingly, a different set of signal transduction components is available as an end-point assay for activation. This allows for assays to be performed in other than the specific host cell from which the protease is derived.

The proteins of the present invention are also useful in competition binding assays in methods designed to discover compounds that interact with the protease (e.g. binding partners and/or ligands). Thus, a compound is exposed to a protease polypeptide under conditions that allow the compound to bind or to otherwise interact with the polypeptide. Soluble protease polypeptide is also added to the mixture. If the test compound interacts with the soluble protease polypeptide, it decreases the amount of complex formed or activity from the protease target. This type of assay is particularly useful in cases in which compounds are sought that interact with specific regions of the protease. Thus, the soluble polypeptide that competes with the target protease region is designed to contain peptide sequences corresponding to the region of interest.

To perform cell free drug screening assays, it is sometimes desirable to immobilize either the protease protein, or fragment, or its target molecule to facilitate separation of complexes from uncomplexed forms of one or both of the proteins, as well as to accommodate automation of the assay.

Techniques for immobilizing proteins on matrices can be used in the drug screening assays. In one embodiment, a fusion protein can be provided which adds a domain that allows the protein to be bound to a matrix. For example, glutathione-S-transferase fusion proteins can be adsorbed onto glutathione sepharose beads (Sigma Chemical, St. Louis, Mo.) or glutathione derivatized microtitre plates, which are then combined with the cell lysates (e.g., $^{35}$S-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes are dissociated. Alternatively, the complexes can be dissociated from the matrix, separated by SDS-PAGE, and the level of protease-binding protein found in the bead fraction quantitated from the gel using standard electrophoretic techniques. For example, either the polypeptide or its target molecule can be immobilized utilizing conjugation of biotin and streptavidin using techniques well known in the art. Alternatively, antibodies reactive with the protein but which do not interfere with binding of the protein to its target molecule can be derivatized to the wells of the plate, and the protein trapped in the wells by antibody conjugation. Preparations of a protease-binding protein and a candidate compound are incubated in the protease protein-presenting wells and the amount of complex trapped in the well can be quantitated. Methods for detecting such complexes, in addition to those described above for the GST-immobilized complexes, include immunodetection of complexes using antibodies reactive with the protease protein target molecule, or which are reactive with protease protein and compete with the target molecule, as well as enzyme-linked assays which rely on detecting an enzymatic activity associated with the target molecule.

Agents that modulate one of the proteases of the present invention can be identified using one or more of the above assays, alone or in combination. It is generally preferable to use a cell-based or cell free system first and then confirm activity in an animal or other model system. Such model systems are well known in the art and can readily be employed in this context.

Modulators of protease protein activity identified according to these drug screening assays can be used to treat a subject with a disorder mediated by the protease pathway, by treating cells or tissues that express the protease. Experimental data as provided in FIG. 1 indicates expression in the human fetus, pooled human melanocyte tissue, fetal heart, and pregnant uterus. These methods of treatment include the steps of administering a modulator of protease activity in a pharmaceutical composition to a subject in need of such treatment, the modulator being identified as described herein.

In yet another aspect of the invention, the protease proteins can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent WO94/10300), to identify other proteins, which bind to or interact with the protease and are involved in protease activity. Such protease-binding proteins are also likely to be involved in the propagation of signals by the protease proteins or protease targets as, for example, downstream elements of a protease-mediated signaling pathway. Alternatively, such protease-binding proteins are likely to be protease inhibitors.

The two-hybrid system is based on the modular nature of most transcription factors, which consist of separable DNA-binding and activation domains. Briefly, the assay utilizes two different DNA constructs. In one construct, the gene that codes for a protease protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a protease-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the protease protein.

This invention further pertains to novel agents identified by the above-described screening assays. Accordingly, it is within the scope of this invention to further use an agent identified as described herein in an appropriate animal model. For example, an agent identified as described herein (e.g., a protease-modulating agent, an antisense protease nucleic acid molecule, a protease-specific antibody, or a protease-binding partner) can be used in an animal or other model to determine the efficacy, toxicity, or side effects of treatment with such an agent. Alternatively, an agent identified as described herein can be used in an animal or other model to determine the mechanism of action of such an agent. Furthermore, this invention pertains to uses of novel agents identified by the above-described screening assays for treatments as described herein.

The protease proteins of the present invention are also useful to provide a target for diagnosing a disease or predisposition to disease mediated by the peptide. Accordingly, the invention provides methods for detecting the presence, or levels of, the protein (or encoding mRNA) in a cell, tissue, or organism. Experimental data as provided in FIG. 1 indicates expression in the human fetus, pooled human melanocyte tissue, fetal heart, and pregnant uterus. The method involves contacting a biological sample with a compound capable of interacting with the protease protein such that the interaction can be detected. Such an assay can be provided in a single detection format or a multi-detection format such as an antibody chip array.

One agent for detecting a protein in a sample is an antibody capable of selectively binding to protein. A biological sample includes tissues, cells and biological fluids isolated from a subject, as well as tissues, cells and fluids present within a subject.

The peptides of the present invention also provide targets for diagnosing active protein activity, disease, or predisposition to disease, in a patient having a variant peptide, particularly activities and conditions that are known for other members of the family of proteins to which the present one belongs. Thus, the peptide can be isolated from a biological sample and assayed for the presence of a genetic mutation that results in aberrant peptide. This includes amino acid substitution, deletion, insertion, rearrangement, (as the result of aberrant splicing events), and inappropriate post-translational modification. Analytic methods include altered electrophoretic mobility, altered tryptic peptide digest, altered protease activity in cell-based or cell-free assay, alteration in substrate or antibody-binding pattern, altered isoelectric point, direct amino acid sequencing, and any other of the known assay techniques useful for detecting mutations in a protein. Such an assay can be provided in a single detection format or a multi-detection format such as an antibody chip array.

In vitro techniques for detection of peptide include enzyme linked immunosorbent assays (ELISAs), Western blots, immunoprecipitations and immunofluorescence using a detection reagent, such as an antibody or protein binding agent. Alternatively, the peptide can be detected in vivo in a subject by introducing into the subject a labeled anti-peptide antibody or other types of detection agent. For example, the antibody can be labeled with a radioactive marker whose presence and location in a subject can be detected by standard imaging techniques. Particularly useful are methods that detect the allelic variant of a peptide expressed in a subject and methods which detect fragments of a peptide in a sample.

The peptides are also useful in pharmacogenomic analysis. Pharmacogenomics deal with clinically significant hereditary variations in the response to drugs due to altered drug disposition and abnormal action in affected persons. See, e.g., Eichelbaum, M. (*Clin. Exp. Pharmacol. Physiol.* 23(10–11):983–985 (1996)), and Linder, M. W. (*Clin. Chem.* 43(2):254–266 (1997)). The clinical outcomes of these variations result in severe toxicity of therapeutic drugs in certain individuals or therapeutic failure of drugs in certain individuals as a result of individual variation in metabolism. Thus, the genotype of the individual can determine the way a therapeutic compound acts on the body or the way the body metabolizes the compound. Further, the activity of drug metabolizing enzymes effects both the intensity and duration of drug action. Thus, the pharmacogenomics of the individual permit the selection of effective compounds and effective dosages of such compounds for prophylactic or therapeutic treatment based on the individual's genotype. The discovery of genetic polymorphisms in some drug metabolizing enzymes has explained why some patients do not obtain the expected drug effects, show an exaggerated drug effect, or experience serious toxicity from standard drug dosages. Polymorphisms can be expressed in the phenotype of the extensive metabolizer and the phenotype of the poor metabolizer. Accordingly, genetic polymorphism may lead to allelic protein variants of the protease protein in which one or more of the protease functions in one population is different from those in another population. The peptides thus allow a target to ascertain a genetic predisposition that can affect treatment modality. Thus, in a ligand-based treatment, polymorphism may give rise to amino terminal extracellular domains and/or other substrate-binding regions that are more or less active in substrate binding, and protease activation. Accordingly, substrate dosage would necessarily be modified to maximize the therapeutic effect within a given population containing a polymorphism. As an alternative to genotyping, specific polymorphic peptides could be identified.

The peptides are also useful for treating a disorder characterized by an absence of, inappropriate, or unwanted expression of the protein. Experimental data as provided in FIG. 1 indicates expression in the human fetus, pooled human melanocyte tissue, fetal heart, and pregnant uterus. Accordingly, methods for treatment include the use of the protease protein or fragments.

Antibodies

The invention also provides antibodies that selectively bind to one of the peptides of the present invention, a protein comprising such a peptide, as well as variants and fragments thereof. As used herein, an antibody selectively binds a target peptide when it binds the target peptide and does not significantly bind to unrelated proteins. An antibody is still considered to selectively bind a peptide even if it also binds to other proteins that are not substantially homologous with the target peptide so long as such proteins share homology with a fragment or domain of the peptide target of the antibody. In this case, it would be understood that antibody binding to the peptide is still selective despite some degree of cross-reactivity.

As used herein, an antibody is defined in terms consistent with that recognized within the art: they are multi-subunit proteins produced by a mammalian organism in response to an antigen challenge. The antibodies of the present invention include polyclonal antibodies and monoclonal antibodies, as well as fragments of such antibodies, including, but not limited to, Fab or F(ab')$_2$, and Fv fragments.

Many methods are known for generating and/or identifying antibodies to a given target peptide. Several such methods are described by Harlow, Antibodies, Cold Spring Harbor Press, (1989).

In general, to generate antibodies, an isolated peptide is used as an immunogen and is administered to a mammalian organism, such as a rat, rabbit or mouse. The full-length protein, an antigenic peptide fragment or a fusion protein can be used. Particularly important fragments are those covering functional domains, such as the domains identified in FIG. 2, and domain of sequence homology or divergence amongst the family, such as those that can readily be identified using protein alignment methods and as presented in the Figures.

Antibodies are preferably prepared from regions or discrete fragments of the protease proteins. Antibodies can be prepared from any region of the peptide as described herein. However, preferred regions will include those involved in function/activity and/or protease/binding partner interaction. FIG. 2 can be used to identify particularly important regions while sequence alignment can be used to identify conserved and unique sequence fragments.

An antigenic fragment will typically comprise at least 8 contiguous amino acid residues. The antigenic peptide can comprise, however, at least 10, 12, 14, 16 or more amino acid residues. Such fragments can be selected on a physical property, such as fragments correspond to regions that are located on the surface of the protein, e.g., hydrophilic regions or can be selected based on sequence uniqueness (see FIG. 2).

Detection on an antibody of the present invention can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^3$H.

Antibody Uses

The antibodies can be used to isolate one of the proteins of the present invention by standard techniques, such as affinity chromatography or immunoprecipitation. The antibodies can facilitate the purification of the natural protein from cells and recombinantly produced protein expressed in host cells. In addition, such antibodies are useful to detect the presence of one of the proteins of the present invention in cells or tissues to determine the pattern of expression of the protein among various tissues in an organism and over the course of normal development. Experimental data as provided in FIG. 1 indicates that protease proteins of the present invention are expressed in the human fetus, pooled human melanocyte tissue, fetal heart, and pregnant uterus. Specifically, a virtual northern blot shows expression in the human fetus, pooled human melanocyte tissue, fetal heart, and pregnant uterus. Further, such antibodies can be used to detect protein in situ, in vitro, or in a cell lysate or supernatant in order to evaluate the abundance and pattern of expression. Also, such antibodies can be used to assess abnormal tissue distribution or abnormal expression during development or progression of a biological condition. Antibody detection of circulating fragments of the full length protein can be used to identify turnover.

Further, the antibodies can be used to assess expression in disease states such as in active stages of the disease or in an individual with a predisposition toward disease related to the protein's function. When a disorder is caused by an inappropriate tissue distribution, developmental expression, level of expression of the protein, or expressed/processed form, the antibody can be prepared against the normal protein. Experimental data as provided in FIG. 1 indicates expression in the human fetus, pooled human melanocyte tissue, fetal heart, and pregnant uterus. If a disorder is characterized by a specific mutation in the protein, antibodies specific for this mutant protein can be used to assay for the presence of the specific mutant protein.

The antibodies can also be used to assess normal and aberrant subcellular localization of cells in the various tissues in an organism. Experimental data as provided in FIG. 1 indicates expression in the human fetus, pooled human melanocyte tissue, fetal heart, and pregnant uterus. The diagnostic uses can be applied, not only in genetic testing, but also in monitoring a treatment modality. Accordingly, where treatment is ultimately aimed at correcting expression level or the presence of aberrant sequence and aberrant tissue distribution or developmental expression, antibodies directed against the protein or relevant fragments can be used to monitor therapeutic efficacy.

Additionally, antibodies are useful in pharmacogenomic analysis. Thus, antibodies prepared against polymorphic proteins can be used to identify individuals that require modified treatment modalities. The antibodies are also useful as diagnostic tools as an immunological marker for aberrant protein analyzed by electrophoretic mobility, isoelectric point, tryptic peptide digest, and other physical assays known to those in the art.

The antibodies are also useful for tissue typing. Experimental data as provided in FIG. 1 indicates expression in the human fetus, pooled human melanocyte tissue, fetal heart, and pregnant uterus. Thus, where a specific protein has been correlated with expression in a specific tissue, antibodies that are specific for this protein can be used to identify a tissue type.

The antibodies are also useful for inhibiting protein function, for example, blocking the binding of the protease peptide to a binding partner such as a substrate. These uses can also be applied in a therapeutic context in which treatment involves inhibiting the protein's function. An antibody can be used, for example, to block binding, thus modulating (agonizing or antagonizing) the peptides activity. Antibodies can be prepared against specific fragments containing sites required for function or against intact protein that is associated with a cell or cell membrane. See FIG. 2 for structural information relating to the proteins of the present invention.

The invention also encompasses kits for using antibodies to detect the presence of a protein in a biological sample. The kit can comprise antibodies such as a labeled or labelable antibody and a compound or agent for detecting protein in a biological sample; means for determining the amount of protein in the sample; means for comparing the amount of protein in the sample with a standard; and instructions for use. Such a kit can be supplied to detect a single protein or epitope or can be configured to detect one of a multitude of epitopes, such as in an antibody detection array. Arrays are described in detail below for nuleic acid arrays and similar methods have been developed for antibody arrays.

Nucleic Acid Molecules

The present invention further provides isolated nucleic acid molecules that encode a protease peptide or protein of the present invention (cDNA, transcript and genomic sequence). Such nucleic acid molecules will consist of, consist essentially of, or comprise a nucleotide sequence that encodes one of the protease peptides of the present invention, an allelic variant thereof, or an ortholog or paralog thereof.

As used herein, an "isolated" nucleic acid molecule is one that is separated from other nucleic acid present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. However, there can be some flanking nucleotide sequences, for example up to about 5 KB, 4 KB, 3 KB, 2 KB, or 1 KB or less, particularly contiguous peptide encoding sequences and peptide encoding sequences within the same gene but separated by introns in the genomic sequence. The important point is that the nucleic acid is isolated from remote and unimportant flanking sequences such that it can be subjected to the specific manipulations described herein such as recombinant expression, preparation of probes and primers, and other uses specific to the nucleic acid sequences.

Moreover, an "isolated" nucleic acid molecule, such as a transcript/cDNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated.

For example, recombinant DNA molecules contained in a vector are considered isolated. Further examples of isolated DNA molecules include recombinant DNA molecules maintained in heterologous host cells or purified (partially or substantially) DNA molecules in solution. Isolated RNA molecules include in vivo or in vitro RNA transcripts of the isolated DNA molecules of the present invention. Isolated nucleic acid molecules according to the present invention further include such molecules produced synthetically.

Accordingly, the present invention provides nucleic acid molecules that consist of the nucleotide sequence shown in FIGS. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists of a nucleotide sequence when the nucleotide sequence is the complete nucleotide sequence of the nucleic acid molecule.

The present invention further provides nucleic acid molecules that consist essentially of the nucleotide sequence shown in FIGS. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists essentially of a nucleotide sequence when such a nucleotide sequence is present with only a few additional nucleic acid residues in the final nucleic acid molecule.

The present invention further provides nucleic acid molecules that comprise the nucleotide sequences shown in FIGS. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule comprises a nucleotide sequence when the nucleotide sequence is at least part of the final nucleotide sequence of the nucleic acid molecule. In such a fashion, the nucleic acid molecule can be only the nucleotide sequence or have additional nucleic acid residues, such as nucleic acid residues that are naturally associated with it or heterologous nucleotide sequences. Such a nucleic acid molecule can have a few additional nucleotides or can comprises several hundred or more additional nucleotides. A brief description of how various types of these nucleic acid molecules can be readily made/isolated is provided below.

In FIGS. 1 and 3, both coding and non-coding sequences are provided. Because of the source of the present invention, humans genomic sequence (FIG. 3) and cDNA/transcript sequences (FIG. 1), the nucleic acid molecules in the Figures will contain genomic intronic sequences, 5' and 3' non-coding sequences, gene regulatory regions and non-coding intergenic sequences. In general such sequence features are either noted in FIGS. 1 and 3 or can readily be identified using computational tools known in the art. As discussed below, some of the non-coding regions, particularly gene regulatory elements such as promoters, are useful for a variety of purposes, e.g. control of heterologous gene expression, target for identifying gene activity modulating compounds, and are particularly claimed as fragments of the genomic sequence provided herein.

The isolated nucleic acid molecules can encode the mature protein plus additional amino or carboxyl-terminal amino acids, or amino acids interior to the mature peptide (when the mature form has more than one peptide chain, for instance). Such sequences may play a role in processing of a protein from precursor to a mature form, facilitate protein trafficking, prolong or shorten protein half-life or facilitate manipulation of a protein for assay or production, among other things. As generally is the case in situ, the additional amino acids may be processed away from the mature protein by cellular enzymes.

As mentioned above, the isolated nucleic acid molecules include, but are not limited to, the sequence encoding the protease peptide alone, the sequence encoding the mature peptide and additional coding sequences, such as a leader or secretory sequence (e.g., a pre-pro or pro-protein sequence), the sequence encoding the mature peptide, with or without the additional coding sequences, plus additional non-coding sequences, for example introns and non-coding 5' and 3' sequences such as transcribed but non-translated sequences that play a role in transcription, mRNA processing (including splicing and polyadenylation signals), ribosome binding and stability of mRNA. In addition, the nucleic acid molecule may be fused to a marker sequence encoding, for example, a peptide that facilitates purification.

Isolated nucleic acid molecules can be in the form of RNA, such as mRNA, or in the form DNA, including cDNA and genomic DNA obtained by cloning or produced by chemical synthetic techniques or by a combination thereof. The nucleic acid, especially DNA, can be double-stranded or single-stranded. Single-stranded nucleic acid can be the coding strand (sense strand) or the non-coding strand (antisense strand).

The invention further provides nucleic acid molecules that encode fragments of the peptides of the present invention as well as nucleic acid molecules that encode obvious variants of the protease proteins of the present invention that are described above. Such nucleic acid molecules may be naturally occurring, such as allelic variants (same locus), paralogs (different locus), and orthologs (different organism), or may be constructed by recombinant DNA methods or by chemical synthesis. Such non-naturally occurring variants may be made by mutagenesis techniques, including those applied to nucleic acid molecules, cells, or organisms. Accordingly, as discussed above, the variants can contain nucleotide substitutions, deletions, inversions and insertions. Variation can occur in either or both the coding and non-coding regions. The variations can produce both conservative and non-conservative amino acid substitutions.

The present invention further provides non-coding fragments of the nucleic acid molecules provided in FIGS. 1 and 3. Preferred non-coding fragments include, but are not limited to, promoter sequences, enhancer sequences, gene modulating sequences and gene termination sequences. Such fragments are useful in controlling heterologous gene expression and in developing screens to identify gene-modulating agents. A promoter can readily be identified as being 5' to the ATG start site in the genomic sequence provided in FIG. 3.

A fragment comprises a contiguous nucleotide sequence greater than 12 or more nucleotides. Further, a fragment could at least 30, 40, 50, 100, 250 or 500 nucleotides in length. The length of the fragment will be based on its intended use. For example, the fragment can encode epitope bearing regions of the peptide, or can be useful as DNA probes and primers. Such fragments can be isolated using the known nucleotide sequence to synthesize an oligonucleotide probe. A labeled probe can then be used to screen a cDNA library, genomic DNA library, or mRNA to isolate nucleic acid corresponding to the coding region. Further, primers can be used in PCR reactions to clone specific regions of gene.

A probe/primer typically comprises substantially a purified oligonucleotide or oligonucleotide pair. The oligonucleotide typically comprises a region of nucleotide sequence that hybridizes under stringent conditions to at least about 12, 20, 25, 40, 50 or more consecutive nucleotides.

Orthologs, homologs, and allelic variants can be identified using methods well known in the art. As described in the Peptide Section, these variants comprise a nucleotide sequence encoding a peptide that is typically 60–70%, 70–80%, 80–90%, and more typically at least about 90–95% or more homologous to the nucleotide sequence shown in the Figure sheets or a fragment of this sequence. Such nucleic acid molecules can readily be identified as being able to hybridize under moderate to stringent conditions, to the nucleotide sequence shown in the Figure sheets or a fragment of the sequence. Allelic variants can readily be determined by genetic locus of the encoding gene.

As used herein, the term "hybridizes under stringent conditions" is intended to describe conditions for hybridization and washing under which nucleotide sequences encoding a peptide at least 60–70% homologous to each other typically remain hybridized to each other. The conditions can be such that sequences at least about 60%, at least about 70%, or at least about 80% or more homologous to each other typically remain hybridized to each other. Such stringent conditions are known to those skilled in the art and can be found in Current Protocols in Molecular Biology, John Wiley & Sons, N.Y. (1989), 6.3.1–6.3.6. One example of stringent hybridization conditions are hybridization in 6× sodium chloride/sodium citrate (SSC) at about 45C., followed by one or more washes in 0.2×SSC, 0.1% SDS at 50–65C. Examples of moderate to low stringency hybridization conditions are well known in the art.

Nucleic Acid Molecule Uses

The nucleic acid molecules of the present invention are useful for probes, primers, chemical intermediates, and in biological assays. The nucleic acid molecules are useful as a hybridization probe for messenger RNA, transcript/cDNA and genomic DNA to isolate full-length cDNA and genomic clones encoding the peptide described in FIG. 2 and to isolate cDNA and genomic clones that correspond to variants (alleles, orthologs, etc.) producing the same or related peptides shown in FIG. 2.

The probe can correspond to any sequence along the entire length of the nucleic acid molecules provided in the Figures. Accordingly, it could be derived from 5' noncoding regions, the coding region, and 3' noncoding regions. However, as discussed, fragments are not to be construed as encompassing fragments disclosed prior to the present invention.

The nucleic acid molecules are also useful as primers for PCR to amplify any given region of a nucleic acid molecule and are useful to synthesize antisense molecules of desired length and sequence.

The nucleic acid molecules are also useful for constructing recombinant vectors. Such vectors include expression vectors that express a portion of, or all of, the peptide sequences. Vectors also include insertion vectors, used to integrate into another nucleic acid molecule sequence, such as into the cellular genome, to alter in situ expression of a gene and/or gene product. For example, an endogenous coding sequence can be replaced via homologous recombination with all or part of the coding region containing one or more specifically introduced mutations.

The nucleic acid molecules are also useful for expressing antigenic portions of the proteins.

The nucleic acid molecules are also useful as probes for determining the chromosomal positions of the nucleic acid molecules by means of in situ hybridization methods.

The nucleic acid molecules are also useful in making vectors containing the gene regulatory regions of the nucleic acid molecules of the present invention.

The nucleic acid molecules are also useful for designing ribozymes corresponding to all, or a part, of the mRNA produced from the nucleic acid molecules described herein.

The nucleic acid molecules are also useful for making vectors that express part, or all, of the peptides.

The nucleic acid molecules are also useful for constructing host cells expressing a part, or all, of the nucleic acid molecules and peptides.

The nucleic acid molecules are also useful for constructing transgenic animals expressing all, or a part, of the nucleic acid molecules and peptides.

The nucleic acid molecules are also useful as hybridization probes for determining the presence, level, form and distribution of nucleic acid expression. Experimental data as provided in FIG. 1 indicates that protease proteins of the present invention are expressed in the human fetus, pooled human melanocyte tissue, fetal heart, and pregnant uterus. Specifically, a virtual northern blot shows expression in the human fetus, pooled human melanocyte tissue, fetal heart, and pregnant uterus. Accordingly, the probes can be used to detect the presence of, or to determine levels of, a specific nucleic acid molecule in cells, tissues, and in organisms. The nucleic acid whose level is determined can be DNA or RNA. Accordingly, probes corresponding to the peptides described herein can be used to assess expression and/or gene copy number in a given cell, tissue, or organism. These uses are relevant for diagnosis of disorders involving an increase or decrease in protease protein expression relative to normal results.

In vitro techniques for detection of mRNA include Northern hybridizations and in situ hybridizations. In vitro techniques for detecting DNA includes Southern hybridizations and in situ hybridization.

Probes can be used as a part of a diagnostic test kit for identifying cells or tissues that express a protease protein, such as by measuring a level of a protease-encoding nucleic acid in a sample of cells from a subject e.g., mRNA or genomic DNA, or determining if a protease gene has been mutated. Experimental data as provided in FIG. 1 indicates that protease proteins of the present invention are expressed in the human fetus, pooled human melanocyte tissue, fetal heart, and pregnant uterus. Specifically, a virtual northern blot shows expression in the human fetus, pooled human melanocyte tissue, fetal heart, and pregnant uterus.

Nucleic acid expression assays are useful for drug screening to identify compounds that modulate protease nucleic acid expression.

The invention thus provides a method for identifying a compound that can be used to treat a disorder associated with nucleic acid expression of the protease gene, particularly biological and pathological processes that are mediated by the protease in cells and tissues that express it. Experimental data as provided in FIG. 1 indicates expression in the human fetus, pooled human melanocyte tissue, fetal heart, and pregnant uterus. The method typically includes assaying the ability of the compound to modulate the expression of the protease nucleic acid and thus identifying a compound that can be used to treat a disorder characterized by undesired protease nucleic acid expression. The assays can be performed in cell-based and cell-free systems. Cell-based assays include cells naturally expressing the protease nucleic acid or recombinant cells genetically engineered to express specific nucleic acid sequences.

The assay for protease nucleic acid expression can involve direct assay of nucleic acid levels, such as mRNA levels, or on collateral compounds involved in the signal pathway. Further, the expression of genes that are up- or down-regulated in response to the protease protein signal pathway can also be assayed. In this embodiment the regulatory regions of these genes can be operably linked to a reporter gene such as luciferase.

Thus, modulators of protease gene expression can be identified in a method wherein a cell is contacted with a candidate compound and the expression of mRNA determined. The level of expression of protease mRNA in the presence of the candidate compound is compared to the level of expression of protease mRNA in the absence of the candidate compound. The candidate compound can then be identified as a modulator of nucleic acid expression based on this comparison and be used, for example to treat a disorder characterized by aberrant nucleic acid expression. When expression of mRNA is statistically significantly greater in the presence of the candidate compound than in its absence, the candidate compound is identified as a stimulator of nucleic acid expression. When nucleic acid expression is statistically significantly less in the presence of the candidate compound than in its absence, the candidate compound is identified as an inhibitor of nucleic acid expression.

The invention further provides methods of treatment, with the nucleic acid as a target, using a compound identified through drug screening as a gene modulator to modulate protease nucleic acid expression in cells and tissues that express the protease. Experimental data as provided in FIG.

1 indicates that protease proteins of the present invention are expressed in the human fetus, pooled human melanocyte tissue, fetal heart, and pregnant uterus. Specifically, a virtual northern blot shows expression in the human fetus, pooled human melanocyte tissue, fetal heart, and pregnant uterus. Modulation includes both up-regulation (i.e. activation or agonization) or down-regulation (suppression or antagonization) or nucleic acid expression.

Alternatively, a modulator for protease nucleic acid expression can be a small molecule or drug identified using the screening assays described herein as long as the drug or small molecule inhibits the protease nucleic acid expression in the cells and tissues that express the protein. Experimental data as provided in FIG. 1 indicates expression in the human fetus, pooled human melanocyte tissue, fetal heart, and pregnant uterus.

The nucleic acid molecules are also useful for monitoring the effectiveness of modulating compounds on the expression or activity of the protease gene in clinical trials or in a treatment regimen. Thus, the gene expression pattern can serve as a barometer for the continuing effectiveness of treatment with the compound, particularly with compounds to which a patient can develop resistance. The gene expression pattern can also serve as a marker indicative of a physiological response of the affected cells to the compound. Accordingly, such monitoring would allow either increased administration of the compound or the administration of alternative compounds to which the patient has not become resistant. Similarly, if the level of nucleic acid expression falls below a desirable level, administration of the compound could be commensurately decreased.

The nucleic acid molecules are also useful in diagnostic assays for qualitative changes in protease nucleic acid expression, and particularly in qualitative changes that lead to pathology. The nucleic acid molecules can be used to detect mutations in protease genes and gene expression products such as mRNA. The nucleic acid molecules can be used as hybridization probes to detect naturally occurring genetic mutations in the protease gene and thereby to determine whether a subject with the mutation is at risk for a disorder caused by the mutation. Mutations include deletion, addition, or substitution of one or more nucleotides in the gene, chromosomal rearrangement, such as inversion or transposition, modification of genomic DNA, such as aberrant methylation patterns or changes in gene copy number, such as amplification. Detection of a mutated form of the protease gene associated with a dysfunction provides a diagnostic tool for an active disease or susceptibility to disease when the disease results from overexpression, underexpression, or altered expression of a protease protein.

Individuals carrying mutations in the protease gene can be detected at the nucleic acid level by a variety of techniques. Genomic DNA can be analyzed directly or can be amplified by using PCR prior to analysis. RNA or cDNA can be used in the same way. In some uses, detection of the mutation involves the use of a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al., *Science* 241:1077–1080 (1988); and Nakazawa et al., *PNAS* 91:360–364 (1994)), the latter of which can be particularly useful for detecting point mutations in the gene (see Abravaya et al., *Nucleic Acids Res.* 23:675–682 (1995)). This method can include the steps of collecting a sample of cells from a patient, isolating nucleic acid (e.g., genomic, mRNA or both) from the cells of the sample, contacting the nucleic acid sample with one or more primers which specifically hybridize to a gene under conditions such that hybridization and amplification of the gene (if present) occurs, and detecting the presence or absence of an amplification product, or detecting the size of the amplification product and comparing the length to a control sample. Deletions and insertions can be detected by a change in size of the amplified product compared to the normal genotype. Point mutations can be identified by hybridizing amplified DNA to normal RNA or antisense DNA sequences.

Alternatively, mutations in a protease gene can be directly identified, for example, by alterations in restriction enzyme digestion patterns determined by gel electrophoresis.

Further, sequence-specific ribozymes (U.S. Pat. No. 5,498,531) can be used to score for the presence of specific mutations by development or loss of a ribozyme cleavage site. Perfectly matched sequences can be distinguished from mismatched sequences by nuclease cleavage digestion assays or by differences in melting temperature.

Sequence changes at specific locations can also be assessed by nuclease protection assays such as RNase and S1 protection or the chemical cleavage method. Furthermore, sequence differences between a mutant protease gene and a wild-type gene can be determined by direct DNA sequencing. A variety of automated sequencing procedures can be utilized when performing the diagnostic assays (Naeve, C. W., (1995) *Biotechniques* 19:448), including sequencing by mass spectrometry (see, e.g., PCT International Publication No. WO 94/16101; Cohen et al., *Adv. Chromatogr.* 36:127–162 (1996); and Griffin et al., *Appl. Biochem. Biotechnol.* 38:147–159 (1993)).

Other methods for detecting mutations in the gene include methods in which protection from cleavage agents is used to detect mismatched bases in RNA/RNA or RNA/DNA duplexes (Myers et al., *Science* 230:1242 (1985)); Cotton et al., *PNAS* 85:4397 (1988); Saleeba et al., *Meth. Enzymol.* 217:286–295 (1992)), electrophoretic mobility of mutant and wild type nucleic acid is compared (Orita et al., *PNAS* 86:2766 (1989); Cotton et al., *Mutat. Res.* 285:125–144 (1993); and Hayashi et al., *Genet. Anal. Tech. Appl.* 9:73–79 (1992)), and movement of mutant or wild-type fragments in polyacrylamide gels containing a gradient of denaturant is assayed using denaturing gradient gel electrophoresis (Myers et al., *Nature* 313:495 (1985)). Examples of other techniques for detecting point mutations include selective oligonucleotide hybridization, selective amplification, and selective primer extension.

The nucleic acid molecules are also useful for testing an individual for a genotype that while not necessarily causing the disease, nevertheless affects the treatment modality. Thus, the nucleic acid molecules can be used to study the relationship between an individual's genotype and the individual's response to a compound used for treatment (pharmacogenomic relationship). Accordingly, the nucleic acid molecules described herein can be used to assess the mutation content of the protease gene in an individual in order to select an appropriate compound or dosage regimen for treatment.

Thus nucleic acid molecules displaying genetic variations that affect treatment provide a diagnostic target that can be used to tailor treatment in an individual. Accordingly, the production of recombinant cells and animals containing these polymorphisms allow effective clinical design of treatment compounds and dosage regimens.

The nucleic acid molecules are thus useful as antisense constructs to control protease gene expression in cells, tissues, and organisms. A DNA antisense nucleic acid molecule is designed to be complementary to a region of the gene involved in transcription, preventing transcription and hence production of protease protein. An antisense RNA or DNA nucleic acid molecule would hybridize to the mRNA and thus block translation of mRNA into protease protein.

Alternatively, a class of antisense molecules can be used to inactivate mRNA in order to decrease expression of protease nucleic acid. Accordingly, these molecules can treat a disorder characterized by abnormal or undesired protease nucleic acid expression. This technique involves cleavage by means of ribozymes containing nucleotide sequences complementary to one or more regions in the mRNA that attenuate the ability of the mRNA to be translated. Possible regions include coding regions and particularly coding regions corresponding to the catalytic and other functional activities of the protease protein, such as substrate binding.

The nucleic acid molecules also provide vectors for gene therapy in patients containing cells that are aberrant in protease gene expression. Thus, recombinant cells, which include the patient's cells that have been engineered ex vivo and returned to the patient, are introduced into an individual where the cells produce the desired protease protein to treat the individual.

The invention also encompasses kits for detecting the presence of a protease nucleic acid in a biological sample. Experimental data as provided in FIG. 1 indicates that protease proteins of the present invention are expressed in the human fetus, pooled human melanocyte tissue, fetal heart, and pregnant uterus. Specifically, a virtual northern blot shows expression in the human fetus, pooled human melanocyte tissue, fetal heart, and pregnant uterus. For example, the kit can comprise reagents such as a labeled or labelable nucleic acid or agent capable of detecting protease nucleic acid in a biological sample; means for determining the amount of protease nucleic acid in the sample; and means for comparing the amount of protease nucleic acid in the sample with a standard. The compound or agent can be packaged in a suitable container. The kit can further comprise instructions for using the kit to detect protease protein mRNA or DNA.

Nucleic Acid Arrays

The present invention further provides nucleic acid detection kits, such as arrays or microarrays of nucleic acid molecules that are based on the sequence information provided in FIGS. 1 and 3 (SEQ ID NOS:1 and 3).

As used herein "Arrays" or "Microarrays" refers to an array of distinct polynucleotides or oligonucleotides synthesized on a substrate, such as paper, nylon or other type of membrane, filter, chip, glass slide, or any other suitable solid support. In one embodiment, the microarray is prepared and used according to the methods described in U.S. Pat. No. 5,837,832, Chee et al., PCT application WO95/11995 (Chee et al.), Lockhart, D. J. et al. (1996; Nat. Biotech. 14: 1675–1680) and Schena, M. et al. (1996; Proc. Natl. Acad. Sci. 93: 10614–10619), all of which are incorporated herein in their entirety by reference. In other embodiments, such arrays are produced by the methods described by Brown et al., U.S. Pat. No. 5,807,522.

The microarray or detection kit is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and most preferably about 20–25 nucleotides in length. For a certain type of microarray or detection kit, it may be preferable to use oligonucleotides that are only 7–20 nucleotides in length. The microarray or detection kit may contain oligonucleotides that cover the known 5', or 3', sequence, sequential oligonucleotides which cover the full length sequence; or unique oligonucleotides selected from particular areas along the length of the sequence. Polynucleotides used in the microarray or detection kit may be oligonucleotides that are specific to a gene or genes of interest.

In order to produce oligonucleotides to a known sequence for a microarray or detection kit, the gene(s) of interest (or an ORF identified from the contigs of the present invention) is typically examined using a computer algorithm which starts at the 5' or at the 3' end of the nucleotide sequence. Typical algorithms will then identify oligomers of defined length that are unique to the gene, have a GC content within a range suitable for hybridization, and lack predicted secondary structure that may interfere with hybridization. In certain situations it may be appropriate to use pairs of oligonucleotides on a microarray or detection kit. The "pairs" will be identical, except for one nucleotide that preferably is located in the center of the sequence. The second oligonucleotide in the pair (mismatched by one) serves as a control. The number of oligonucleotide pairs may range from two to one million. The oligomers are synthesized at designated areas on a substrate using a light-directed chemical process. The substrate may be paper, nylon or other type of membrane, filter, chip, glass slide or any other suitable solid support.

In another aspect, an oligonucleotide may be synthesized on the surface of the substrate by using a chemical coupling procedure and an ink jet application apparatus, as described in PCT application WO95/251116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536, 6144 or more oligonucleotides, or any other number between two and one million which lends itself to the efficient use of commercially available instrumentation.

In order to conduct sample analysis using a microarray or detection kit, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray or detection kit so that the probe sequences hybridize to complementary oligonucleotides of the microarray or detection kit. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray or detection kit. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for largescale correlation studies on the sequences, expression patterns, mutations, variants, or polymorphisms among samples.

Using such arrays, the present invention provides methods to identify the expression of the protease proteins/peptides of the present invention. In detail, such methods comprise incubating a test sample with one or more nucleic acid molecules and assaying for binding of the nucleic acid molecule with components within the test sample. Such assays will typically involve arrays comprising many genes, at least one of which is a gene of the present invention and or alleles of the protease gene of the present invention.

Conditions for incubating a nucleic acid molecule with a test sample vary. Incubation conditions depend on the format employed in the assay, the detection methods employed, and the type and nature of the nucleic acid molecule used in the assay. One skilled in the art will recognize that any one of the commonly available hybridization, amplification or array assay formats can readily be adapted to employ the novel fragments of the Human genome disclosed herein. Examples of such assays can be found in Chard, T, *An Introduction to Radioimmunoassay and Related Techniques*, Elsevier Science Publishers, Amsterdam, The Netherlands (1986); Bullock, G. R. et al., *Techniques in Immunocytochemistry*, Academic Press, Orlando, Fla. Vol. 1 (1982), Vol. 2 (1983), Vol. 3 (1985); Tijssen, P., *Practice and Theory of Enzyme Immunoassays: Laboratory Techniques in Biochemistry and Molecular Biology*, Elsevier Science Publishers, Amsterdam, The Netherlands (1985).

The test samples of the present invention include cells, protein or membrane extracts of cells. The test sample used in the above-described method will vary based on the assay format, nature of the detection method and the tissues, cells or extracts used as the sample to be assayed. Methods for preparing nucleic acid extracts or of cells are well known in the art and can be readily be adapted in order to obtain a sample that is compatible with the system utilized.

In another embodiment of the present invention, kits are provided which contain the necessary reagents to carry out the assays of the present invention.

Specifically, the invention provides a compartmentalized kit to receive, in close confinement, one or more containers which comprises: (a) a first container comprising one of the nucleic acid molecules that can bind to a fragment of the Human genome disclosed herein; and (b) one or more other containers comprising one or more of the following: wash reagents, reagents capable of detecting presence of a bound nucleic acid.

In detail, a compartmentalized kit includes any kit in which reagents are contained in separate containers. Such containers include small glass containers, plastic containers, strips of plastic, glass or paper, or arraying material such as silica. Such containers allows one to efficiently transfer reagents from one compartment to another compartment such that the samples and reagents are not cross-contaminated, and the agents or solutions of each container can be added in a quantitative fashion from one compartment to another. Such containers will include a container which will accept the test sample, a container which contains the nucleic acid probe, containers which contain wash reagents (such as phosphate buffered saline, Tris-buffers, etc.), and containers which contain the reagents used to detect the bound probe. One skilled in the art will readily recognize that the previously unidentified protease gene of the present invention can be routinely identified using the sequence information disclosed herein can be readily incorporated into one of the established kit formats which are well known in the art, particularly expression arrays.

Vectors/Host Cells

The invention also provides vectors containing the nucleic acid molecules described herein. The term "vector" refers to a vehicle, preferably a nucleic acid molecule, which can transport the nucleic acid molecules. When the vector is a nucleic acid molecule, the nucleic acid molecules are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, OR MAC.

A vector can be maintained in the host cell as an extra-chromosomal element where it replicates and produces additional copies of the nucleic acid molecules. Alternatively, the vector may integrate into the host cell genome and produce additional copies of the nucleic acid molecules when the host cell replicates.

The invention provides vectors for the maintenance (cloning vectors) or vectors for expression (expression vectors) of the nucleic acid molecules. The vectors can function in prokaryotic or eukaryotic cells or in both (shuttle vectors).

Expression vectors contain cis-acting regulatory regions that are operably linked in the vector to the nucleic acid molecules such that transcription of the nucleic acid molecules is allowed in a host cell. The nucleic acid molecules can be introduced into the host cell with a separate nucleic acid molecule capable of affecting transcription. Thus, the second nucleic acid molecule may provide a trans-acting factor interacting with the cis-regulatory control region to allow transcription of the nucleic acid molecules from the vector. Alternatively, a trans-acting factor may be supplied by the host cell. Finally, a trans-acting factor can be produced from the vector itself. It is understood, however, that in some embodiments, transcription and/or translation of the nucleic acid molecules can occur in a cell-free system.

The regulatory sequence to which the nucleic acid molecules described herein can be operably linked include promoters for directing mRNA transcription. These include, but are not limited to, the left promoter from bacteriophage λ, the lac, TRP, and TAC promoters from *E. coli*, the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region a ribosome binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al., *Molecular Cloning: A Laboratory Manual. 2nd. ed.*, Cold Spring Harbor Laboratory Press, Cold Spring Harbor, N.Y., (1989).

A variety of expression vectors can be used to express a nucleic acid molecule. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, poxviruses, pseudorabies viruses, and retroviruses. Vectors may also be derived from combinations of these sources such as those derived from plasmid and bacteriophage genetic elements, e.g. cosmids and phagemids. Appropriate cloning and expression vectors for prokaryotic and eukaryotic hosts are described in Sambrook et al., *Molecular Cloning: A Laboratory Manual. 2nd. ed.*, Cold Spring Harbor Laboratory Press, Cold Spring Harbor, N.Y., (1989).

The regulatory sequence may provide constitutive expression in one or more host cells (i.e. tissue specific) or may provide for inducible expression in one or more cell types such as by temperature, nutrient additive, or exogenous factor such as a hormone or other ligand. A variety of vectors providing for constitutive and inducible expression in prokaryotic and eukaryotic hosts are well known to those of ordinary skill in the art.

The nucleic acid molecules can be inserted into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate nucleic acid molecule can be introduced into an appropriate host cell for propagation or expression using well-known techniques. Bacterial cells include, but are not limited to, *E. coli, Streptomyces*, and *Salmonella typhimurium*. Eukaryotic cells include, but are not limited to, yeast, insect cells such as *Drosophila*, animal cells such as COS and CHO cells, and plant cells.

As described herein, it may be desirable to express the peptide as a fusion protein. Accordingly, the invention provides fusion vectors that allow for the production of the peptides. Fusion vectors can increase the expression of a recombinant protein, increase the solubility of the recombinant protein, and aid in the purification of the protein by acting for example as a ligand for affinity purification. A proteolytic cleavage site may be introduced at the junction of the fusion moiety so that the desired peptide can ultimately be separated from the fusion moiety. Proteolytic enzymes include, but are not limited to, factor Xa, thrombin, and enteroprotease. Typical fusion expression vectors include pGEX (Smith et al., *Gene* 67:31–40 (1988)), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Examples of suitable inducible non-fusion *E. coli* expression vectors include pTrc (Amann et al., *Gene* 69:301–315 (1988)) and pET 11d (Studier et al., *Gene Expression Technology: Methods in Enzymology* 185:60–89 (1990)).

Recombinant protein expression can be maximized in host bacteria by providing a genetic background wherein the host cell has an impaired capacity to proteolytically cleave the recombinant protein. (Gottesman, S., *Gene Expression Technology: Methods in Enzymology* 185, Academic Press, San Diego, Calif. (1990) 119–128). Alternatively, the sequence of the nucleic acid molecule of interest can be altered to provide preferential codon usage for a specific host cell, for example *E. coli*. (Wada et al., *Nucleic Acids Res.* 20:2111–2118 (1992)).

The nucleic acid molecules can also be expressed by expression vectors that are operative in yeast. Examples of vectors for expression in yeast e.g., *S. cerevisiae* include pYepSec1 (Baldari, et al., *EMBO J.* 6:229–234 (1987)), pMFa (Kuijan et al., *Cell* 30:933–943(1982)), pJRY88 (Schultz et al., *Gene* 54:113–123 (1987)), and pYES2 (Invitrogen Corporation, San Diego, Calif.).

The nucleic acid molecules can also be expressed in insect cells using, for example, baculovirus expression vectors. Baculovirus vectors available for expression of proteins in cultured insect cells (e.g., Sf9 cells) include the pAc series (Smith et al., *Mol. Cell Biol.* 3:2156–2165 (1983)) and the pVL series (Lucklow et al., *Virology* 170:31–39 (1989)).

In certain embodiments of the invention, the nucleic acid molecules described herein are expressed in mammalian cells using mammalian expression vectors. Examples of mammalian expression vectors include pCDM8 (Seed, B. *Nature* 329:840(1987)) and pMT2PC (Kaufman et al., *EMBO J.* 6:187–195 (1987)).

The expression vectors listed herein are provided by way of example only of the well-known vectors available to those of ordinary skill in the art that would be useful to express the nucleic acid molecules. The person of ordinary skill in the art would be aware of other vectors suitable for maintenance propagation or expression of the nucleic acid molecules described herein. These are found for example in Sambrook, J., Fritsh, E. F., and Maniatis, T. *Molecular Cloning: A Laboratory Manual. 2nd, ed.*, Cold Spring Harbor Laboratory, Cold Spring Harbor Laboratory Press, Cold Spring Harbor, N.Y., 1989.

The invention also encompasses vectors in which the nucleic acid sequences described herein are cloned into the vector in reverse orientation, but operably linked to a regulatory sequence that permits transcription of antisense RNA. Thus, an antisense transcript can be produced to all, or to a portion, of the nucleic acid molecule sequences described herein, including both coding and non-coding regions. Expression of this antisense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include prokaryotic cells, lower eukaryotic cells such as yeast, other eukaryotic cells such as insect cells, and higher eukaryotic cells such as mammalian cells.

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook, et al. (*Molecular Cloning: A Laboratory Manual. 2nd, ed., Cold Spring Harbor Laboratory*, Cold Spring Harbor Laboratory Press, Cold Spring Harbor, N.Y., 1989).

Host cells can contain more than one vector. Thus, different nucleotide sequences can be introduced on different vectors of the same cell. Similarly, the nucleic acid molecules can be introduced either alone or with other nucleic acid molecules that are not related to the nucleic acid molecules such as those providing trans-acting factors for expression vectors. When more than one vector is introduced into a cell, the vectors can be introduced independently, co-introduced or joined to the nucleic acid molecule vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication will occur in host cells providing functions that complement the defects.

Vectors generally include selectable markers that enable the selection of the subpopulation of cells that contain the recombinant vector constructs. The marker can be contained in the same vector that contains the nucleic acid molecules described herein or may be on a separate vector. Markers include tetracycline or ampicillin-resistance genes for prokaryotic host cells and dihydrofolate reductase or neomycin resistance for eukaryotic host cells. However, any marker that provides selection for a phenotypic trait will be effective.

While the mature proteins can be produced in bacteria, yeast, mammalian cells, and other cells under the control of the appropriate regulatory sequences, cell-free transcription and translation systems can also be used to produce these proteins using RNA derived from the DNA constructs described herein.

Where secretion of the peptide is desired, which is difficult to achieve with multi-transmembrane domain containing proteins such as proteases, appropriate secretion signals are incorporated into the vector. The signal sequence can be endogenous to the peptides or heterologous to these peptides.

Where the peptide is not secreted into the medium, which is typically the case with proteases, the protein can be isolated from the host cell by standard disruption procedures, including freeze thaw, sonication, mechanical disruption, use of lysing agents and the like. The peptide can then be recovered and purified by well-known purification methods including ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that depending upon the host cell in recombinant production of the peptides described herein, the peptides can have various glycosylation patterns, depending upon the cell, or maybe non-glycosylated as when produced in bacteria. In addition, the peptides may include an initial modified methionine in some cases as a result of a host-mediated process.

Uses of Vectors and Host Cells

The recombinant host cells expressing the peptides described herein have a variety of uses. First, the cells are useful for producing a protease protein or peptide that can be further purified to produce desired amounts of protease protein or fragments. Thus, host cells containing expression vectors are useful for peptide production.

Host cells are also useful for conducting cell-based assays involving the protease protein or protease protein fragments, such as those described above as well as other formats known in the art. Thus, a recombinant host cell expressing a native protease protein is useful for assaying compounds that stimulate or inhibit protease protein function.

Host cells are also useful for identifying protease protein mutants in which these functions are affected. If the mutants naturally occur and give rise to a pathology, host cells containing the mutations are useful to assay compounds that have a desired effect on the mutant protease protein (for example, stimulating or inhibiting function) which may not be indicated by their effect on the native protease protein.

Genetically engineered host cells can be further used to produce non-human transgenic animals. A transgenic animal is preferably a mammal, for example a rodent, such as a rat or mouse, in which one or more of the cells of the animal include a transgene. A transgene is exogenous DNA which is integrated into the genome of a cell from which a transgenic animal develops and which remains in the genome of the mature animal in one or more cell types or tissues of the transgenic animal. These animals are useful for studying the function of a protease protein and identifying and evaluating modulators of protease protein activity. Other examples of transgenic animals include non-human primates, sheep, dogs, cows, goats, chickens, and amphibians.

A transgenic animal can be produced by introducing nucleic acid into the male pronuclei of a fertilized oocyte, e.g., by microinjection, retroviral infection, and allowing the oocyte to develop in a pseudopregnant female foster animal. Any of the protease protein nucleotide sequences can be introduced as a transgene into the genome of a non-human animal, such as a mouse.

Any of the regulatory or other sequences useful in expression vectors can form part of the transgenic sequence. This includes intronic sequences and polyadenylation signals, if not already included. A tissue-specific regulatory sequence(s) can be operably linked to the transgene to direct expression of the protease protein to particular cells.

Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of transgenic mRNA in tissues or cells of the animals. A transgenic founder animal can then be used to breed additional animals carrying the transgene. Moreover, transgenic animals carrying a transgene can further be bred to other transgenic animals carrying other transgenes. A transgenic animal also includes animals in which the entire animal or tissues in the animal have been produced using the homologously recombinant host cells described herein.

In another embodiment, transgenic non-human animals can be produced which contain selected systems that allow for regulated expression of the transgene. One example of such a system is the cre/loxP recombinase system of bacteriophage P1. For a description of the cre/loxP recombinase system, see, e.g., Lakso et al. *PNAS* 89:6232–6236 (1992). Another example of a recombinase system is the FLP recombinase system of *S. cerevisiae* (O'Gorman et al. *Science* 251:1351–1355 (1991). If a cre/loxP recombinase system is used to regulate expression of the transgene, animals containing transgenes encoding both the Cre recombinase and a selected protein is required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. *Nature* 385:810–813 (1997) and PCT International Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to pseudopregnant female foster animal. The offspring born of this female foster animal will be a clone of the animal from which the cell, e.g., the somatic cell, is isolated.

Transgenic animals containing recombinant cells that express the peptides described herein are useful to conduct the assays described herein in an in vivo context. Accordingly, the various physiological factors that are present in vivo and that could effect substrate binding, protease protein activity/activation, and signal transduction, may not be evident from in vitro cell-free or cell-based assays. Accordingly, it is useful to provide non-human transgenic animals to assay in vivo protease protein function, including substrate interaction, the effect of specific mutant protease proteins on protease protein function and substrate interaction, and the effect of chimeric protease proteins. It is also possible to assess the effect of null mutations, that is mutations that substantially or completely eliminate one or more protease protein functions.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the above-described modes for carrying out the invention which are obvious to those skilled in the field of molecular biology or related fields are intended to be within the scope of the following claims.

That which is claimed is:

1. An isolated antibody that selectively binds to a polypeptide wherein the amino acid sequence of said polypeptide consists of SEO ID NO:2.

2. An Isolated antibody that selectively binds to a polypeptide, wherein the amino acid sequence of said polypeptide comprises SEQ ID NO:2.

3. The antibody of claim 2, wherein the antibody is a monoclonal antibody.

4. The antibody of claim 3, wherein the antibody is coupled to a detectable substance.

5. A composition comprising the antibody of claim 3 and a pharmaceutically acceptable carrier.

6. The antibody of claim 2, wherein the antibody is coupled to a detectable substance.

7. A composition comprising the antibody of claim 2 and a pharmaceutically acceptable carrier.

8. The antibody of claim 1, wherein the antibody is a monoclonal antibody.

9. The antibody of claim 8, wherein the antibody is coupled to a detectable substance.

10. A composition comprising the antibody of claim 8 and a pharmaceutically acceptable carrier.

11. The antibody of claim 1, wherein the antibody is coupled to a detectable substance.

12. A composition comprising the antibody of claim 1 and a pharmaceutically acceptable carrier.

13. An isolated antibody fragment that selectively binds to apolypeptide, wherein the amino acid sequence of said polypeptide consists of SEQ ID NO:2, and wherein the antibody fragment comprises a fragment selected from the group consisting of:
a) an Fab fragment;
b) an F(ab')$_2$ fragment; and
c) an Fv fragment.

14. An isolated antibody fragment that selectively binds to apolypeptide, wherein the amino acid sequence of said polypeptide composes SEQ ID NO:2, and wherein the antibody fragment comprises a fragment selected from the group consisting of:
a) an Fab fragment;
b) an F(ab')$_2$ fragment; and
c) an Fv fragment.

* * * * *